(12) United States Patent
RayChaudhuri et al.

(10) Patent No.: US 7,575,889 B2
(45) Date of Patent: Aug. 18, 2009

(54) COMPOUND COMBINATIONS FOR INHIBITING CELL DIVISION AND METHODS FOR THEIR IDENTIFICATION AND USE

(75) Inventors: Debrabata RayChaudhuri, Somerville, MA (US); Marc Kirschner, Newton, MA (US)

(73) Assignees: President and Fellows of Harvard College, Cambridge, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 11/376,259

(22) Filed: Mar. 14, 2006

(65) Prior Publication Data

US 2006/0252114 A1 Nov. 9, 2006

Related U.S. Application Data

(63) Continuation-in-part of application No. 10/180,384, filed on Jun. 26, 2002, now Pat. No. 7,011,946, and a continuation-in-part of application No. 10/153,268, filed on May 22, 2002, now abandoned.

(60) Provisional application No. 60/292,883, filed on May 22, 2001, provisional application No. 60/300,931, filed on Jun. 26, 2001, provisional application No. 60/691,092, filed on Jun. 16, 2005.

(51) Int. Cl.
*C12Q 1/18* (2006.01)
(52) U.S. Cl. .......................................... 435/32; 435/7.2
(58) Field of Classification Search .................. 435/3.2, 435/7.2
See application file for complete search history.

(56) References Cited

U.S. PATENT DOCUMENTS

| | | | |
|---|---|---|---|
| 5,948,889 A | 9/1999 | de Boer et al. | |
| 5,976,826 A | 11/1999 | Singhvi et al. | |
| 6,368,838 B1 | 4/2002 | Singhvi et al. | |
| 6,559,176 B1 * | 5/2003 | Bassler et al. | 514/408 |
| 7,011,946 B2 | 3/2006 | RayChaudhuri et al. | |
| 2003/0138869 A1 | 7/2003 | RayChaudhuri et al. | |

FOREIGN PATENT DOCUMENTS

| | | |
|---|---|---|
| EP | 0505023 | 9/1992 |
| EP | 0505023 | 8/1996 |
| WO | WO 01/85664 | 11/2001 |

OTHER PUBLICATIONS

U.S. Appl. No. 09/863,141.
U.S. Appl. No. 10/153,268.
U.S. Appl. No. 10/180,384.
Akiyama, Y., et al., *J. Biol. Chem.* 271:31196-31201, 1996.
Berge, S. M., et al., *J. Pharmaceutical Sciences*, 66: 1-19, 1977.
Breithaupt, H., "The New Antibiotics: Can Novel Anti-bacterial Treatments Combat the Rising Tide of Drug-Resistant Infections?" *Nature Biotechnology*, 17: 1165, 1997.
Lee, et al., *J. Biol. Chem.* 267:1212-1218, 1992.
Movahed, M.R. *J.S.C. Med. Assoc.* 95: 303, 1999.
Murray, B., *New Engl. J. Med.* 330: 1229-1230, 1994.
International Search Report for PCT/US2006/023168, Date of mailing: Apr. 23, 2007.
Written Opinion of International Searching Authority, PCT/US2006/023168, Date of mailing: Apr. 23, 2007.

* cited by examiner

*Primary Examiner*—Chih-Min Kam
(74) *Attorney, Agent, or Firm*—Julie Anne Knight; Brenda Jarrell; Choate, Hall & Stewart, LLP

(57) ABSTRACT

The present invention provides in vitro assays, e.g., FtsZ GTPase assays, and/or in vivo assays and methods of use thereof to identify particular compounds and combinations of compounds that affect microbial cell division. The invention further provides such compounds and compound combinations, including combinations that result in inhibition of cell survival or growth when present together at concentrations below their individual MICs. Certain of the compound combinations display synergism. Certain of the combinations include a compound that inhibits FtsZ GTPase activity and a compound that inhibits cell growth by a mechanism other than inhibition of FtsZ GTPase activity. The present invention further provides pharmaceutical compositions that have antimicrobial activity and methods of treating microbial infections.

6 Claims, 25 Drawing Sheets

FtsZ Rings in Pre-Divisional *E. coli* Cells
IF Image
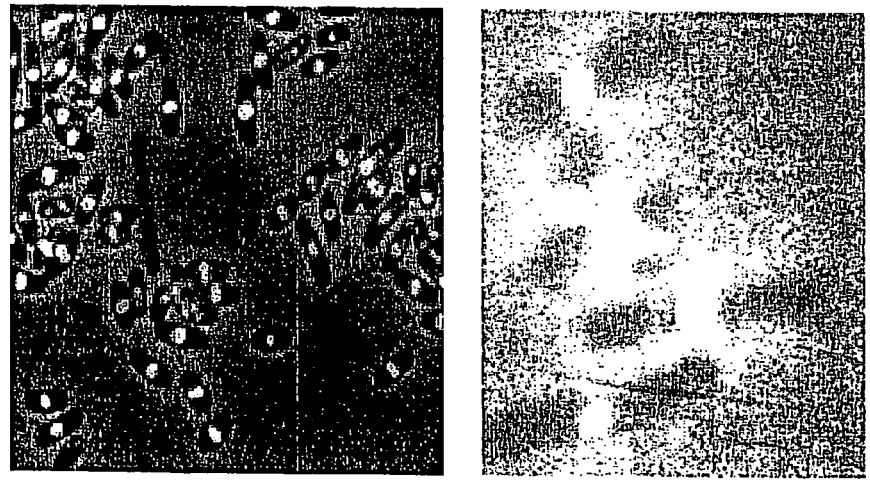
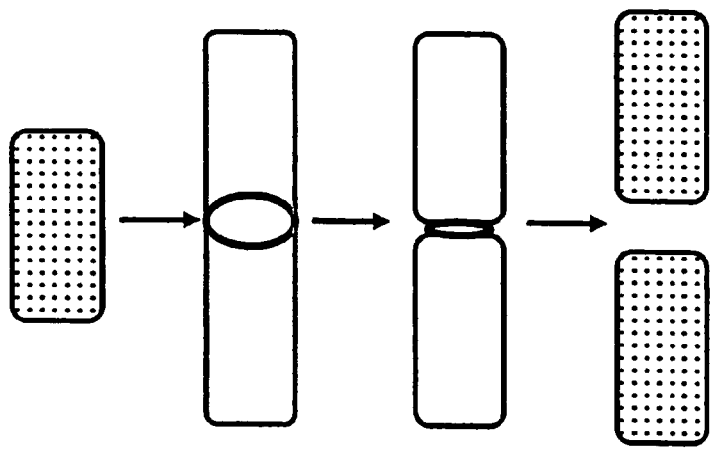
A Cartoon showing FtsZ Ring Constriction in a Rod-Shaped Cell
FIG. 3

Septal Ring Assembly in *E. Coli*

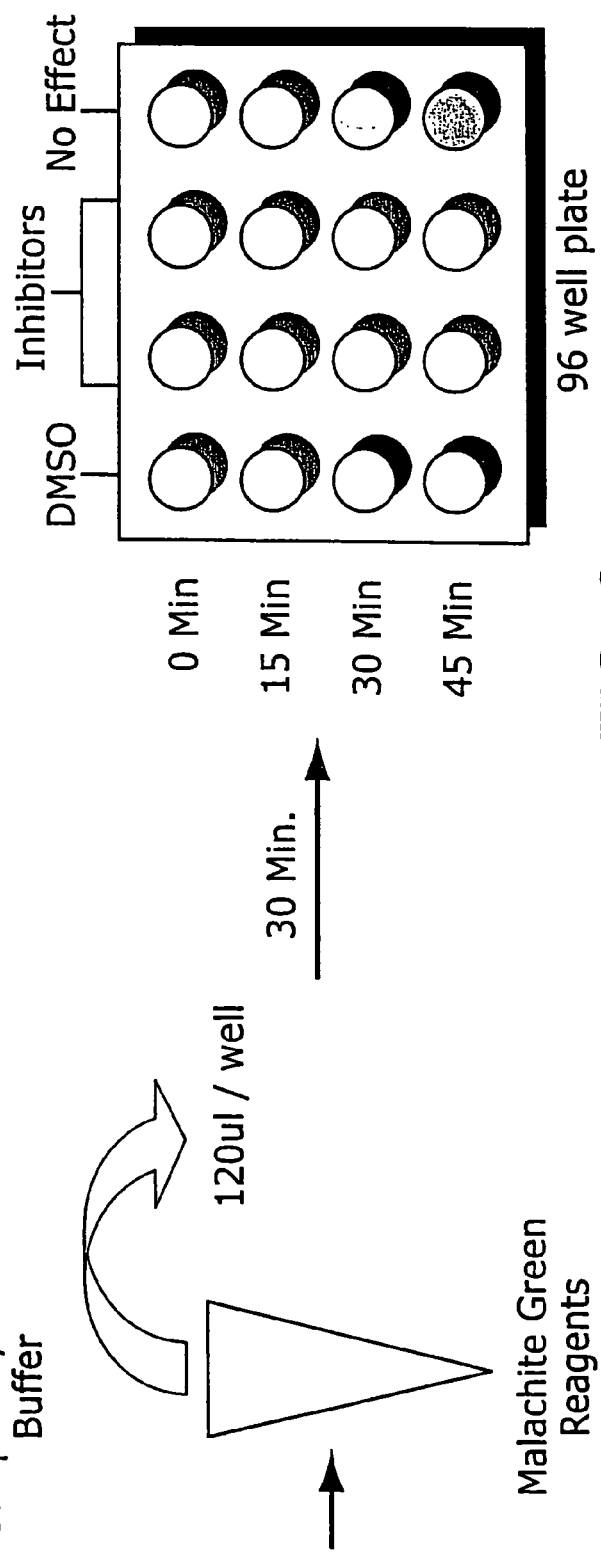
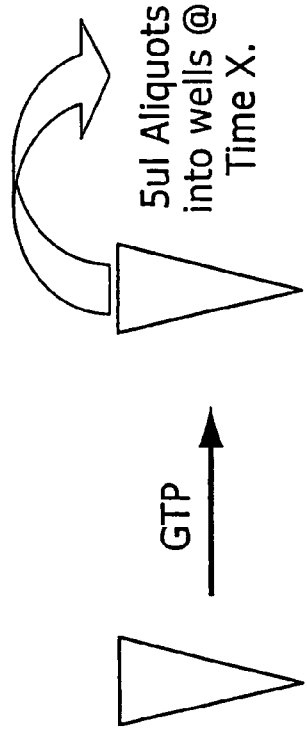
FIG. 9

A Flow Chart of the In Vivo Screen:

18,320 Compounds Screened *in vivo*

→ Hits (45% Inhibition of Cell Growth)

173 Hits: *ftsZ-ts* Mutant
- 52 Filamentation
- 121 Lysis/Change in Cell Shape

98 Hits: Wild-Type *E. coli*
- 18 Filamentation
- 80 Lysis/Change in Cell Shape

FIG. 10

Five Hits From *In Vitro* FtsZ Screen
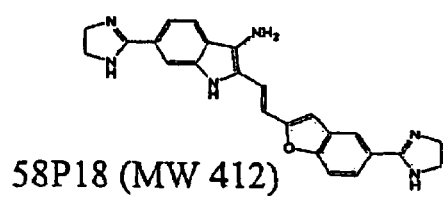
58P18 (MW 412)
27F02 (MW 488)
27D12 (MW 410)
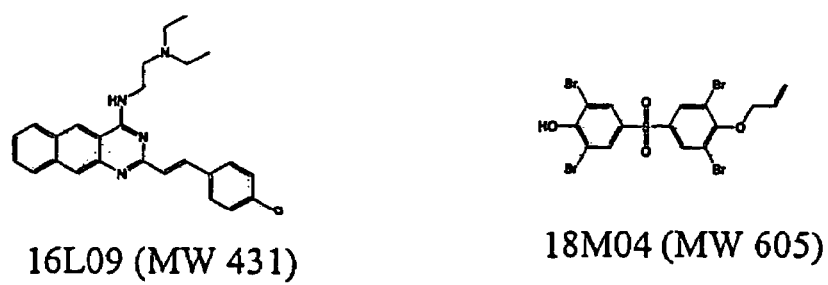
16L09 (MW 431)
18M04 (MW 605)
FIG. 11

Five Hits From *In Vivo* FtsZ Screen
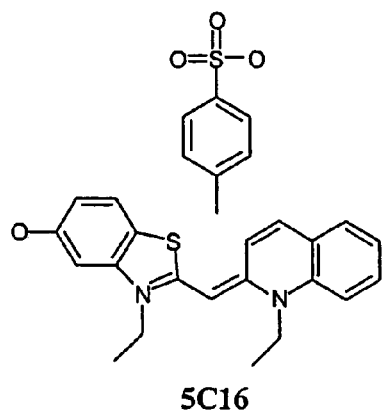
5C16
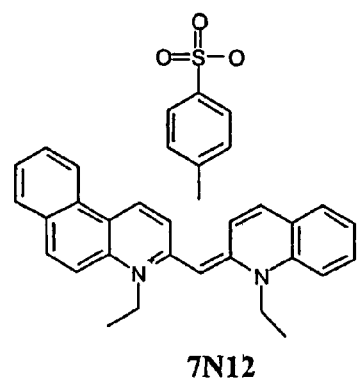
7N12
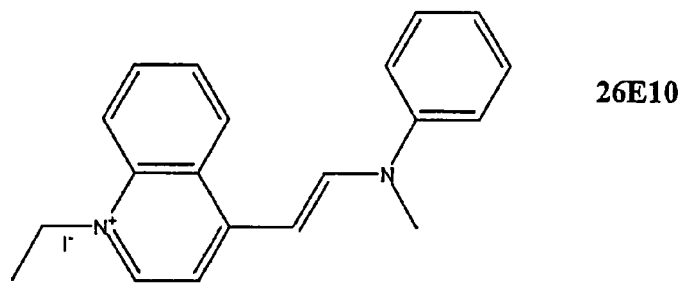
26E10
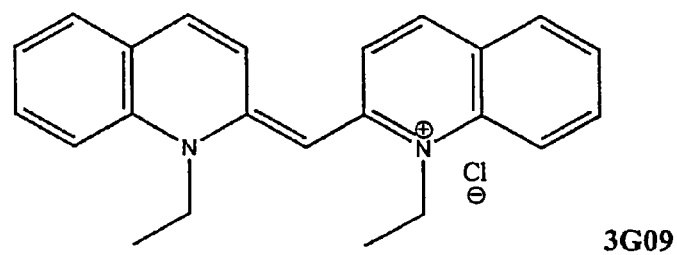
3G09
FIG. 16

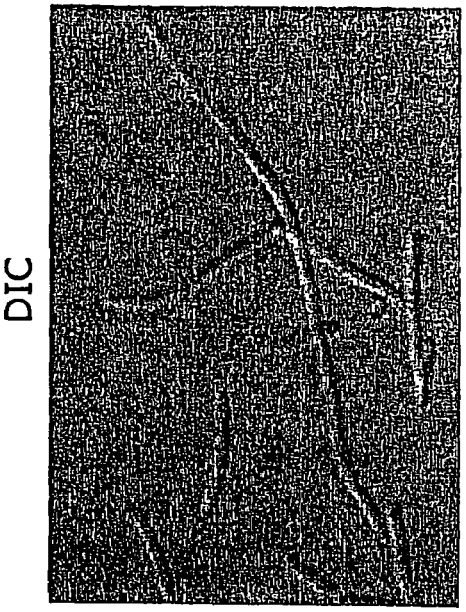
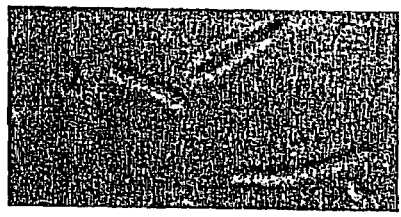
**26E-10 on FtsZ Ring Assembly in AcrAB Pump-Negative *E. coli***
DIC
FtsZ -GFP
26E-10 (10 μM) 90 min
FIG. 18

Minimum Inhibitory Concentrations (MICs; μM) of FtsZ GTPase Inhibitors Identified *In Vitro*

| Organism | 27D12 | 27F02 | 16L09 | 18M04 | 58P18 |
|---|---|---|---|---|---|
| *Escherichia coli* MC 1000 | 20 | 40 | >80 | >80 | >80 |
| *E. coli* DRC 39 (ΔacrAB::Tn903kan$^r$)* | 20 | 5 | 10 | >80 | 80§ |
| *E. coli* DRC 40 (ΔacrAB::Tn903kan$^r$ ftsZ84-ts)* | 40 | 5 | 10 | >80 | 80¶ |
| *E. coli* DRC 42 (ΔacrAB::Tn903kan$^r$ recA::cat)* | 20 | 5 | 5 | >80 | 80* |
| *Shigella dysenteriae* 60R | 10 | 10 | 20 | >80 | >80 |
| *Vibrio cholerae* N16961 | 5 | 5 | 5 | >80 | >80 |
| *Pseudomonas aeruginosa* PAK | 40 | >80 | >80 | >80 | >80 |
| *Pseudomonas aeruginosa* (ΔmexAB)⁼ | 40 | >80 | >80 | >80 | >80 |
| *Bacillus subtilis* JH 642 | 1.25 | 2.5 | 2.5 | 2.5 | 40 |
| *Bacillus cereus* CIP 3852 | 0.625 | 5 | 20 | 2.5 | 80 |
| *Staphylococcus aureus* H | 2.5 | 1.25 | 5 | 10 | >80 |
| *Staphylococcus aureus* MRSA‡ | 2.5 | 2.5 | 10 | 10 | >80 |
| *Streptococcus pneumoniae* TIGR 4 | 0.312 | 2.5 | 5 | 10 | >80 |
| *Clostridium perfringens* Strain 13 | 5 | 10 | 80 | 5 | >80 |

\* DRC 39, DRC 40, and DRC 42 are derivatives of the wild-type *E. coli* strain MC 1000

= ΔmexAB mutant of *P. aeruginosa* is a derivative of the wild-type strain PAK

‡ Methicillin-resistant *S. aureus*, a clinical isolate from Tufts-New England Medical Center § denotes residual turbidity due to unlyzed filaments, filament ghosts, and some short, non-motile cells ¶ faint turbidity, less than in DRC 39; very long filaments, some with increased diameter, filament ghosts and few short cells

FIG. 19

- Cartesian Pin Transfer Robot
- Pin Array
- 384/1536 Well Plates
- Wallac Victor ® Fluorescence Plate-Reader

Exclude:
- 28 Highly Toxic / No Phenotype / No FtsZ Inhibition
- 8 Weak Phenotype and / or Weak Toxicity
- 1 Cipro Analogue
- 1 Carcinogen
- 1 DNA Intercalator
- 1 Not Available

Category 1 (2) – Filamenting phenotype and FtsZ inhibitor.

Category 2 (6) – Filamenting phenotype NOT an FtsZ inhibitor.

Category 3 (4) – FtsZ inhibitor and NO filamenting phenotype.

Category 4 (2) – Round phenotype.

FIG. 23B

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Tubulin signature sequence

<400> SEQUENCE: 1

Gly Gly Gly Thr Gly Ser Gly
1               5

<210> SEQ ID NO 2
<211> LENGTH: 7
<212> TYPE: PRT
<213> ORGANISM: Artificial Sequence
<220> FEATURE:
<223> OTHER INFORMATION: FtsZ signature sequence

<400> SEQUENCE: 2

Gly Gly Gly Thr Gly Thr Gly
```

```
<210> SEQ ID NO 3
<211> LENGTH: 7
<212> TYPE: PRT
<213> ORGANISM: Artificial Sequence
<220> FEATURE:
<223> OTHER INFORMATION: FtsZ signature sequence

<400> SEQUENCE: 3

Ser Gly Gly Thr Gly Thr Gly
1               5
```

COMPOUND COMBINATIONS FOR INHIBITING CELL DIVISION AND METHODS FOR THEIR IDENTIFICATION AND USE

CROSS-REFERENCE TO RELATED APPLICATIONS

This application is a continuation-in-part of U.S. patent application Ser. No. 10/180,384 filed Jun. 26, 2002, now U.S. Pat. No. 7,011,946, which claims priority to and the benefit of U.S. provisional application Ser. No. 60/300,931, filed Jun. 26, 2001 and is a continuation-in-part of U.S. patent application Ser. No. 10/153,268, filed May 22, 2002, now abandoned, which claims priority to and the benefit of U.S. provisional application Ser. No. 60/292,883, filed May 22, 2001. This application also claims priority to and the benefit of U.S. provisional application Ser. No. 60/691,092, filed Jun. 16, 2005. The entire contents of each of these applications are incorporated herein by reference. It is noted that certain information and/or data in the instant specification may supersede information and/or data in the earlier applications, in which case the instant specification will control.

GOVERNMENT SUPPORT

Development of the present invention was funded by a grant from the Department of Defense Advanced Research Projects Agency (Grant Number N65236-98-1-5408). Accordingly, the United States Government may have certain rights in the invention.

BACKGROUND OF THE INVENTION

Anti-microbial agents, such as antibiotics, have been effective tools in the treatment of infectious diseases during the last half-century. The systematic screening of natural product libraries from soil samples or marine environments has generated most of the classes of anti-bacterial agents used today (e.g., β-lactams, aminoglycosides, macrolides, and sulfonamides, to name a few). Additionally, these initial leads have, in many cases, been subsequently modified to produce second and third generation therapeutics with one or more of broadened anti-microbial activity, enhanced oral bioavailability, and improved toxicological and pharmacokinetic properties.

From the time that antibiotic therapy was first developed to the late 1980s, there was almost complete control over bacterial infections in developed countries. However, the emergence of resistant bacteria, especially during the late 1980s and early 1990s, is changing this situation (see, for example, Breithaupt, H., "The New Antibiotics: Can Novel Anti-bacterial Treatments Combat the Rising Tide of Drug-Resistant Infections?" Nature Biotechnology, (1997) 17: 1165). The increase in antibiotic resistant strains has been particularly common in major hospitals and care centers. The consequences of the increase in resistant strains include higher morbidity and mortality, longer patient hospitalization, and an increase in treatment costs. (B. Murray, New Engl. J. Med. 330:1229-1230 (1994)).

One major factor that is contributing to the increase in the number of resistance strains is the over-use and/or inappropriate administration of anti-microbials in the treatment arena. Newly acquired resistance is generally due to the relatively rapid mutation rate in bacteria. Another contributing factor is the ability of many microorganisms to exchange genetic material that confers resistance, e.g., exchanging of resistance plasmids (R plasmids) or resistance transposons.

For example, following years of use to treat various infections and diseases, penicillin resistance has become increasingly widespread in the microbial populations that were previously susceptible to the action of this drug. Some microorganisms produce β-lactamase, an enzyme that destroys the anti-microbial itself, while other microorganisms have undergone genetic changes that result in alterations to the cell receptors known as the penicillin-binding proteins, such that penicillin no longer effectively binds to the receptors. Other organisms have evolved in a manner that prevents the lysis of cells to which the drug has bound. The drug therefore inhibits the growth of the cell, but does not kill the cell. This appears to contribute to the relapse of disease following premature discontinuation of treatment, as some of the cells remain viable and may begin growing once the anti-microbial is removed from their environment.

The first report of penicillin resistance occurred in Australia in 1967. Since this initial report, increasing numbers of penicillin resistant strains have been reported worldwide. In addition, strains having resistance to numerous other antibiotics have also been reported, including strains that are resistant to chloramphenicol, erythromycin, tetracycline, clindamycin, rifampin, and sulfamethoxazole-trimethoprim.

Microorganisms that are resistant to this wide range of drugs include opportunistic and virulent pathogens that were previously susceptible to antibiotic treatment. Resistant opportunistic pathogens are problematic for debilitated or immunocompromised patients, while the development of tolerance and resistance in virulent pathogens poses a significant threat to the ability to treat disease in all patients, compromised and non-compromised. Infections resulting from these naturally resistant opportunistic or virulent pathogens are becoming more difficult to treat with currently available antibiotics.

Clearly, in order to maintain the standard of public health we enjoy today, there is an urgent medical need for the identification of compounds having anti-microbial activity that can override existing mechanisms of resistance. Preferably, the anti-microbial compounds are active against a broad spectrum of microorganisms, while remaining non-toxic to human and other mammalian cells.

SUMMARY OF THE INVENTION

The invention provides in vivo assay systems and methods of using these assay systems for screening compounds for anti-microbial activity. In particular, the present invention provides in vivo assay systems that utilize conditional-lethal and other non-lethal conditional bacterial mutants in target gene products to screen compounds for anti-microbial activity. For example, the present invention provides a phenotypic screen for compounds that inhibit bacterial cell division.

The present invention further provides pharmaceutical compositions including anti-microbial agents and methods of using such pharmaceutical compositions to treat microbial infections and/or disorders related to microbial infections. The compounds can be used in combination with other agents for the prophylaxis and treatment of conditions associated with microbial infections and/or disorders related to microbial infections.

In certain preferred embodiments, microorganisms are not resistant to the identified anti-microbial agents, and/or the agents have a broad spectrum of activity, and/or exhibit improved bioavailability, and/or have minimal side effects. In a particularly preferred embodiment of the invention the compounds are effective against certain microorganisms that are resistant to some or even all of the anti-bacterial agents that are currently approved or in clinical trials.

The pharmaceutical compositions can be used alone or in combination with other agents for the prophylaxis and treatment of conditions associated with microbial infections or disorders related to microbial infections. In general, the inventive compositions comprise an effective amount of an anti-microbial compound or a pharmaceutically acceptable salt thereof, in combination with a pharmaceutically acceptable carrier, such as a diluent or excipient.

In still another aspect, the invention provides methods for prophylaxis and/or treatment of conditions associated with microbial infections and/or disorders related to microbial infections by administering an effective amount of an inventive compound. In particular, the invention provides a method for the treatment or prophylaxis of conditions associated with microbial infections and/or disorders related to microbial infections comprising administering to a host (such as a bird, fish, or cell) or patient, such as a primate, an effective amount of a compound of the present invention.

In certain preferred embodiments combination therapies are provided wherein an effective amount of a compound of the present invention, and an effective amount of one or more other compounds useful in the treatment of conditions associated with microbial infections and/or disorders related to microbial infections, are administered to a host or patient.

In yet another aspect, the present invention also provides pharmaceutical packs or kits comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

The invention further provides novel assays for the identification of agents having anti-microbial activity, e.g., anti-bacterial activity, e.g., activity against any eubacteria or archaebacteria. In particular, these assays inhibit the ubiquitous prokaryotic cell division protein FtsZ. Such anti-microbial agents have the activity of inhibiting cell division by blocking the formation of the FtsZ ring that is crucial for septation. In other embodiments, the identified compounds and compositions may be inhibitory to plastid division in plants and thus be useful to kill undesirable plant species, algae, etc. In various embodiments the identified compounds and compositions may be inhibitory to the division of cells whose organelles (e.g., certain mitochondria, chloroplasts, etc.) contain FtzZ-like proteins that play a role in organelle division.

The invention provides combinations of compounds (e.g., 2, 3, or 4-compound combinations) that are effective to inhibit cell survival and/or growth when used together at concentrations below their minimum inhibitory concentrations (MIC). In other words, each compound is used at a concentration below its MIC, preferably at a concentration in which cells can grow in the presence of the individual compounds without significant effects on culture density. However, when the compounds are provided together at these sub-lethal concentrations, cell survival and/or growth is inhibited. Preferred combinations result in lack of detectable cell growth. Certain preferred combinations include at least one compound that inhibits FtsZ activity, e.g., FtsZ GTPase activity, and at least one compound that inhibits cell division by a mechanism other than inhibiting FtsZ GTPase activity.

The invention further provides methods of identifying preferred combinations of compounds using, for example, the screening assays described herein.

The compounds, compound combinations, and/or methods of the invention may, e.g., inhibit FtsZ activity and/or cell division or any indication(s) thereof (e.g., FtsZ ring assembly, septum formation, etc.) by 10%-100%, e.g., 10%, 20%, 30%, 40%, 50%, 60%, 70%, 80%, 90%, or more.

BRIEF DESCRIPTION OF THE DRAWING

The invention is described with reference to the several Figures of the drawing.

FIG. 3 shows a diagram of an FtsZ ring structure and photographs of an FtsZ ring structure by immunofluorescence in predivisional *E. coli* cells.

FIG. 9 is an illustration of the malachite green assay.

FIG. 10 is a flow chart representing the results of a library screen using an in vivo assay.

FIG. 11 illustrates the chemical structure of various inhibitors of FtsZ GTPase activity identified using in vitro assays. It is noted that the compounds can be provided as salts, and different counterions can be used.

FIG. 16 illustrates the chemical structure of various cell division inhibitors identified using an in vivo screen, including 26E-10, an inhibitor of FtsZ ring assembly. It is noted that the compounds can be provided as salts, and different counterions or molecules with countervailing charges can be employed. For example, the tosyl groups associated with 5C-16 and 7N-12 are not part of the active molecules.

FIG. 18 shows additional images that illustrate the effect of compound 26E-10 on FtsZ ring assembly in *E. coli*.

FIG. 19 is a table illustrating the minimum inhibitory concentrations of FtsZ GTPase inhibitory compounds identified in vitro. The compounds were tested against a variety of gram-negative and gram-positive bacteria.

DEFINITIONS

Figure 1:
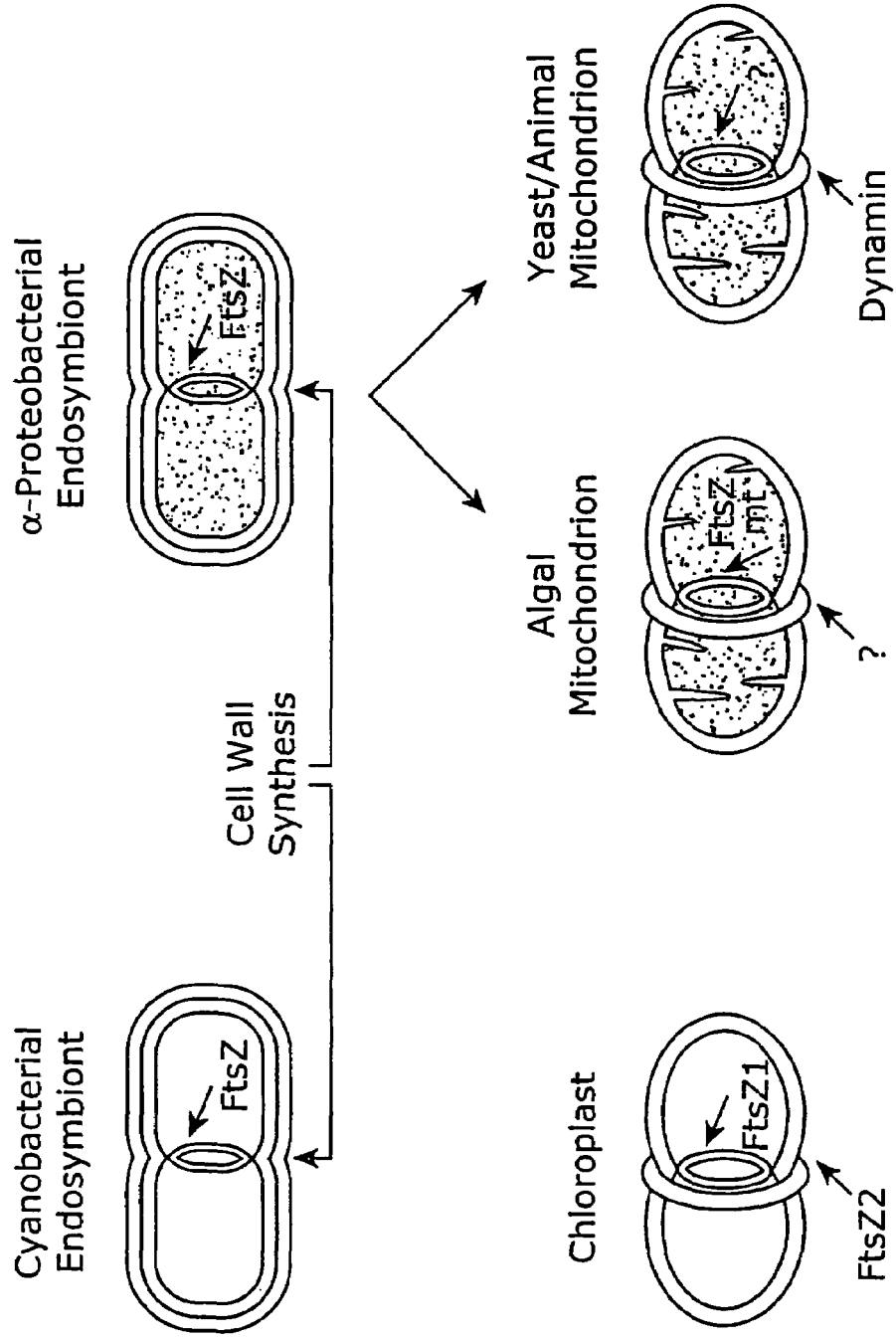
FIG. 1 is a drawing depicting FtsZ mediated cell division in different cell types.

As discussed above, the present invention provides pharmaceutical compositions including compounds useful in the eradication or inactivation (i.e., affect their inability to replicate) of harmful microorganisms prior to infection and thus can be utilized as therapeutic, preventative, and/or disinfectant agents.

It will be appreciated by one of ordinary skill in the art that numerous asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers.

Additionally, the present invention provides pharmaceutically acceptable derivatives of the foregoing compounds, and methods of treating animals, including humans, using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is typically an inactive form of a drug that exerts its effects after processes (e.g., metabolic processes) within the body convert it to a usable or active form. For example, frequently a pro-drug is a derivative of a compound, usually with significantly reduced pharmacological activity, which contains an additional moiety that is susceptible to removal or modification in vivo yielding the parent molecule as the pharmacologically active species. An example of a pro-drug is an ester that is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of and/or prevention of bacterial infections, protozoal infections, or for disorders related to microbial infections. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

Unless otherwise specified, alkyl and other aliphatic groups preferably contain 1-6, or 1-3, contiguous aliphatic carbon atoms. Illustrative aliphatic groups thus include, but are not limited to, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents.

In certain embodiments of the present invention C$_1$-C$_3$ or C$_1$-C$_6$ alkyl moieties are employed. As used herein, the terms "C$_1$-C$_3$-alkyl" and "C$_1$-C$_6$-alkyl" refer to saturated, substituted or unsubstituted, straight- or branched-chain hydrocarbon radicals derived from a hydrocarbon moiety containing between one and three, and one and six carbon atoms, respectively, by removal of a single hydrogen atom. Examples of C$_1$-C$_3$-alkyl radicals include, but are not limited to, methyl, ethyl, propyl and isopropyl. Examples of C$_1$-C$_6$-alkyl radicals include, but are not limited to, methyl, ethyl, propyl, isopropyl, n-butyl, tert-butyl, neopentyl and n-hexyl.

In certain embodiments of the present invention, C$_2$-C$_6$ alkenyl moieties are employed. The term "C$_2$-C$_6$-alkenyl" denotes a monovalent group derived from a hydrocarbon moiety containing from two to six carbon atoms and having at least one carbon-carbon double bond by the removal of a single hydrogen atom. Additionally, the $C_2$-$C_6$ alkenyl moieties, as used herein, may be substituted or unsubstituted. Alkenyl groups include, but are not limited to, for example, ethenyl, propenyl, butenyl, 1-methyl-2-buten-1-yl, and the like.

In certain embodiments of the present invention, $C_2$-$C_6$ alkynyl moieties are employed. The term "$C_1$-$C_6$-alkynyl" as used herein refers to a monovalent group derived from a hydrocarbon containing from two to six carbon atoms and having at least one carbon-carbon triple bond by the removal of a single hydrogen atom. Additionally, the $C_2$-$C_6$ alkenyl moieties, as used herein, may be substituted or unsubstituted. Representative alkynyl groups include, but are not limited to, ethynyl, 2-propynyl (propargyl), 1-propynyl and the like.

The term "$C_1$-$C_6$-alkoxy" as used herein refers to a $C_1$-$C_6$-alkyl group, as previously defined, attached to the parent molecular moiety through an oxygen atom. Examples of $C_1$-$C_6$-alkoxy, but are not limited to, methoxy, ethoxy, propoxy, isopropoxy, n-butoxy, tert-butoxy, neopentoxy and n-hexoxy.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$-$C_3$ alkylamino groups are utilized in the present invention. The term "$C_1$-$C_3$-alkylamino" as used herein refers to one or two $C_1$-$C_3$-alkyl groups, as previously defined, attached to the parent molecular moiety through a nitrogen atom. Examples of $C_1$-$C_3$-alkylamino include, but are not limited to methylamino, dimethylamino, ethylamino, diethylamino, and propylamino. Some examples of substituents of the above-described aliphatic (and other) moieties of compounds of the invention include, but are not limited to: F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl. Additional examples of generally applicable substituents are illustrated by the specific embodiments shown in the Examples that are described herein.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted. F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$- cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substituents are illustrated by the specific embodiments shown in the Examples that are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to: F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl", as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl" group is utilized and as used herein, refers to a heterocycloalkyl group, as defined above, substituted by independent replacement of one, two or three of the hydrogen atoms thereon with but are not limited to: F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, NHCONH-heteroaryl, $SO_2$—$C_1$-$C_6$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl. Additional examples of generally applicable substituents are illustrated by the specific embodiments shown in the Examples that are described herein.

"Hydroxy-protecting group", as used herein, refers to an easily removable group, which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, $2^{nd}$ edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "oxo" denotes a group wherein two hydrogen atoms on a single carbon atom in an alkyl group as defined above are replaced with a single oxygen atom (i.e. a carbonyl group).

The terms "minimal inhibitory concentration" (MIC) and "minimal bactericidal concentration" (MBC) are used herein consistently with their use in the art, i.e., to indicate the concentration of a compound that will inhibit bacterial proliferation (growth) (MIC) or kill bacteria (MBC). The MIC values discussed herein represent $MIC_{99}$ values, i.e., concentrations that reduce bacterial proliferation to 1% or less of the control value that would occur in the absence of the compound. As is well known in the art, MIC and MBC can be measured by a variety of methods, including automated and non-automated methods. Widely used methods include the disk (agar) diffusion (Kirby-Bauer) method and the broth dilution method. The MIC values referred to herein were measured using the standard broth dilution method, but it is to be understood that other methods could also be used.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: Organic Solvents Physical Properties and Methods of Purification, $4^{th}$ ed., edited by John A. Riddick et al., Vol. II, in the Techniques of Chemistry Series, John Wiley & Sons, NY, 1986.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

DRC39 is the MC 1000 (ftsZ+) delta acrAB::kan strain of E. coli.

DRC40 is the DRC13 (ftsZ84) delta acrAB::kan strain of E. coli.

DETAILED DESCRIPTION OF CERTAIN EMBODIMENTS

As discussed above, the invention relates to assay systems and the uses of these assay systems for screening compounds for anti-microbial activity, and more particularly, to using bacterial proteins in vitro or in vivo to detect compounds that interfere with cell division. In one preferred embodiment, the present invention provides in vivo cellular assays that utilize mutant bacterial strains that have a defect in cell division to screen compounds for anti-microbial activity.

The present invention further relates to pharmaceutical compositions including compounds useful in the treatment and/or prevention of one or more microbial infections and to methods of treatment utilizing such compositions. Those skilled in the art will appreciate that this includes compounds that inhibit the growth of microbial cells, such as yeast, fungi, protozoa, bacteria, and the like.

Assay Systems and Methods of Use

Bacterial cells divide by first initiating DNA replication. At the end of the bacterial cell cycle, the chromosomes segregate and the cells divide by forming a septum that divides the cells in two, a process known as septation.

A large collection of mutants that block DNA replication and/or cell division have been identified in a wide range of microbial cells. In many cases, the gene(s) responsible for the mutant phenotypes and their wild-type counterparts have been cloned and characterized. The in vivo and in vitro activities of such wild-type and mutant proteins may be employed to identify inhibitors of DNA replication and/or cell division and thus identify inhibitors of microbial cell growth. Furthermore, a protein that is a key player in one type of microbial cell, for example, a bacterial cell, may be conserved in another type of microbial cell, e.g., a fungal cell. Thus, inhibitors that block the activity of these proteins to prevent cell division might also overlap between different microbial cell types.

Such anti-microbial agents may be used as broad-spectrum therapeutics, e.g., as anti-microbial agents. Alternatively, such anti-microbial agents may be used for decontamination, e.g., decontamination of water having a high microbial count. It may also be appreciated that molecules that activate the activity of a protein involved in the cell cycle may also be identified, which may spur further basic research.

One protein that participates in bacterial cell division is the FtsZ protein. FtsZ is essential for bacterial cell multiplication and is ubiquitous in the prokaryotic kingdom, being present in eubacteria (gram-positive/gram-negative), archaea, mycoplasmas, chloroplasts, and mitochondria of lower eukaryotes), while it is absent from the mitochondria of higher eukaryotes (yeast to humans) and also appears to be absent from the obligate intracellular bacterial pathogen, *Chlamydia trachomatis*. Other potential targets that each harbor a single copy of the ftsZ gene, which is likely to be essential for cell division, include *Vibrio cholerae, Haemophilus influenzae, Staphylococcus aureus, Clostridium perfringens, Mycobacterium tuberculosis, Bacillus anthracis, Francisella tularensis, Shigella flexneri*, and *Brucella abortus*. However, it is to be understood that the compounds and methods of the invention are useful as inhibitors of cell division regardless of the number of ftsZ genes possessed by a particular target organism.

Figure 2:
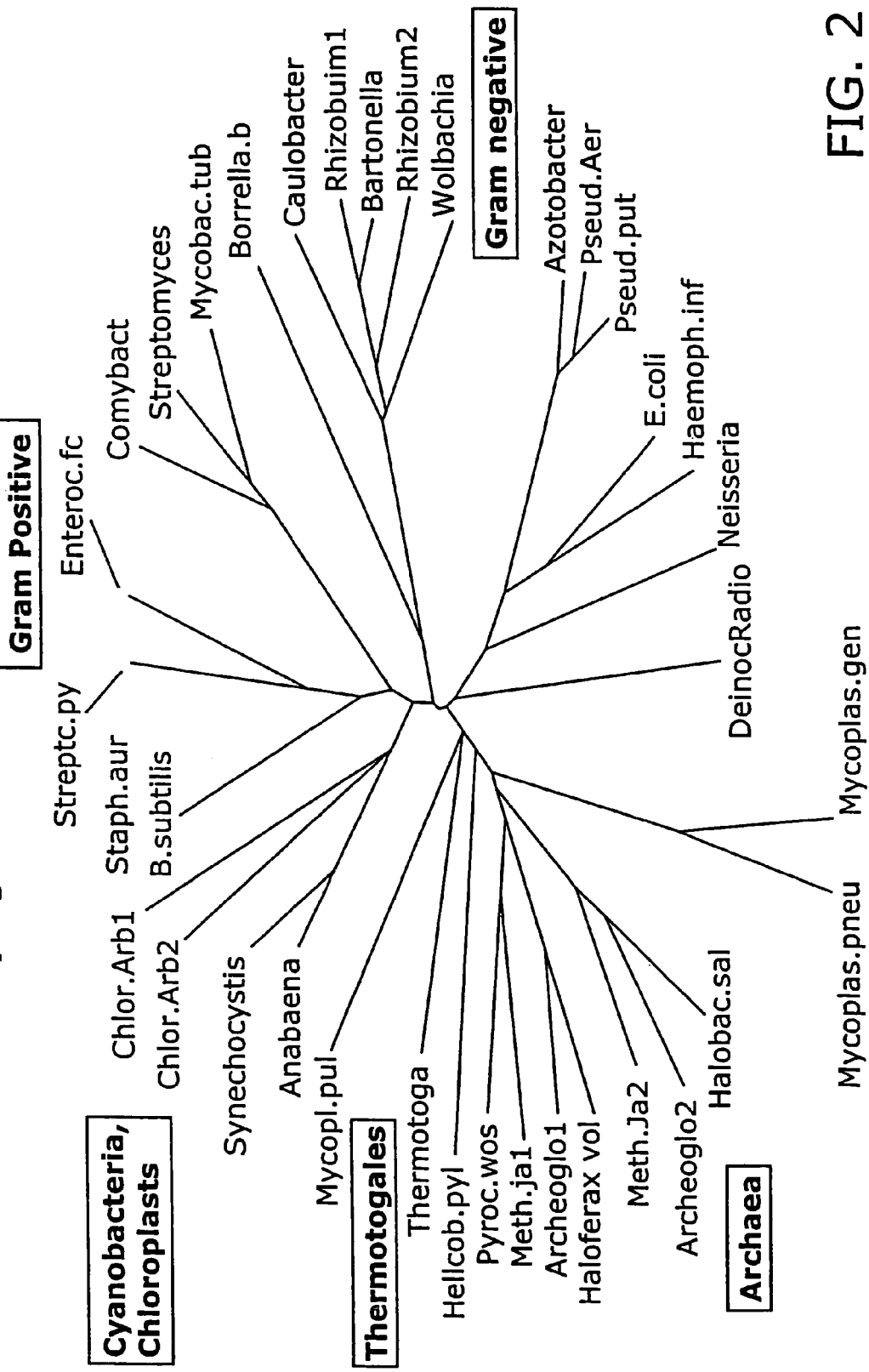
FIG. 2 is a phylogenetic tree of FtsZ orthologs.

The constriction of organelles in cyanobacteria, a-proteobacteria, chloroplast, algea, and yeast or animal mitochondria is depicted in FIG. 1. A phylogenetic tree of FtsZ orthologs that might have FtsZ activity is shown in FIG. 2. Therefore, because inhibitors of FtsZ activity are expected to block cell division in a wide range of prokaryotic organisms, molecules that modulate FtsZ function may be developed as broad-spectrum anti-bacterial agents against known and unknown bacterial pathogens and other pathogenic or undesirable species.

FtsZ is a tubulin-like GTPase that forms a membrane-associated cytokinetic contractile ring structure in vivo at the site of division in bacterial cells (see FIG. 3, which shows localization of FtsZ as the cytokinetic ring structure in predivisional *E. coli* cells). The tubulin signature sequence is GGGTGSG (SEQ ID NO: 1). The FtsZ signature sequence is GGGTGTG (SEQ ID NO: 2). During the process of cell division, FtsZ becomes concentrated at the inner membrane into a ring-like structure at the prospective division site immediately before the start of cell division. During septation, the diameter of the FtsZ ring (also referred to herein as the Z ring) becomes progressively smaller as it remains at the leading edge of the invaginating cell wall.

Figure 4:
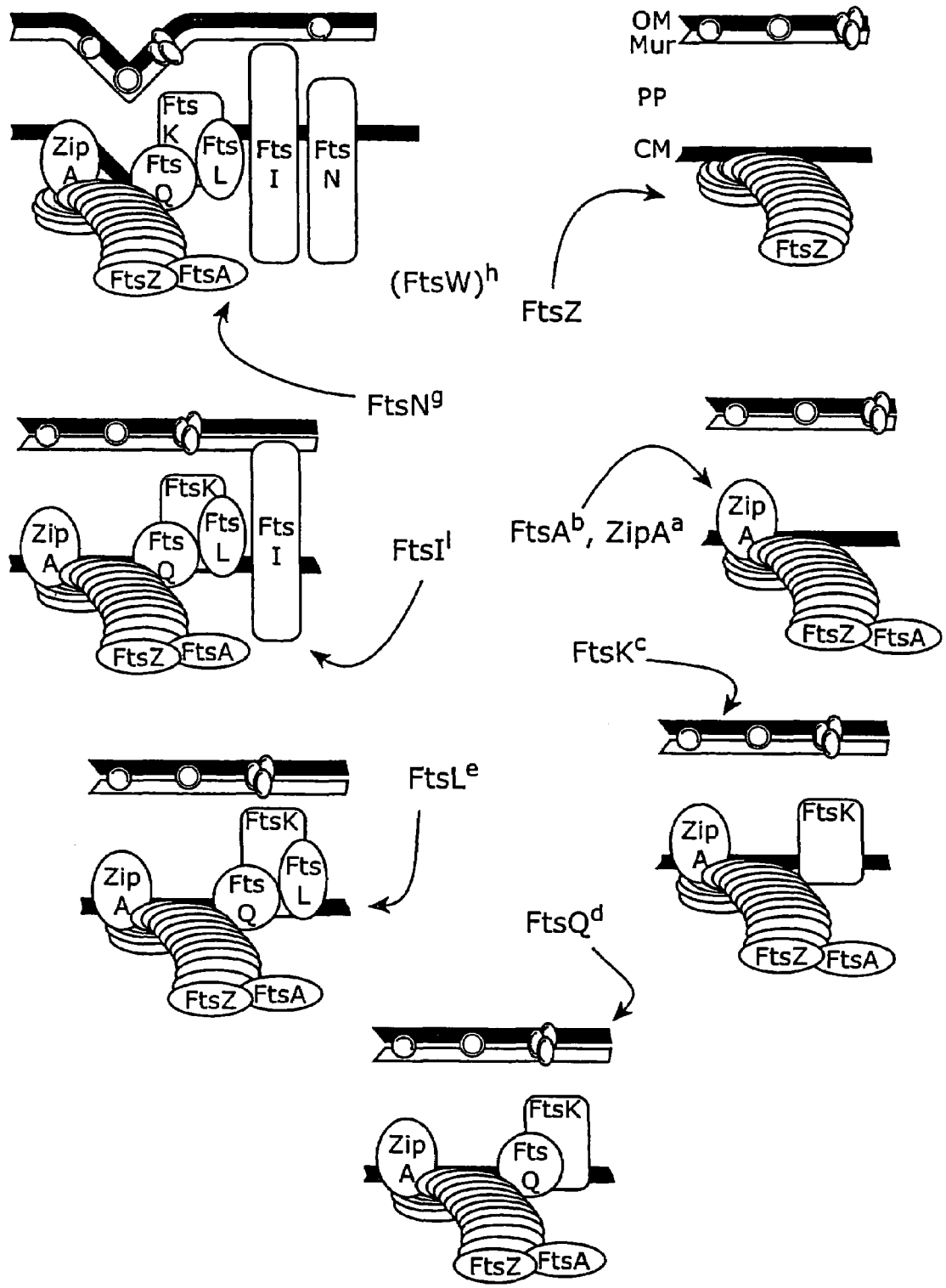
FIG. 4 is a drawing showing proteins involved in septal ring assembly in *E. coli*.

FtsZ is believed to interact with several different molecules that also play specific roles in one or more cell division processes (see FIG. 4). Genetic studies have suggested possible interactions between FtsZ and several other proteins. For example, FtsZ has been shown to interact with FtsA by yeast two-hybrid analysis and by the ability of the FtsZ ring to recruit FtsA. Indeed FtsA can be co-purified with FtsZ and vice-versa. FtsZ also is known to interact with ZipA, a protein essential for cell viability. Cells lacking sufficient ZipA activity die. Thus, those skilled in the art will appreciate that large screens for compounds that either inhibit or activate the ability of FtsZ to interact with FtsA or ZipA have great flexibility in their design and implementation.

Figure 5:
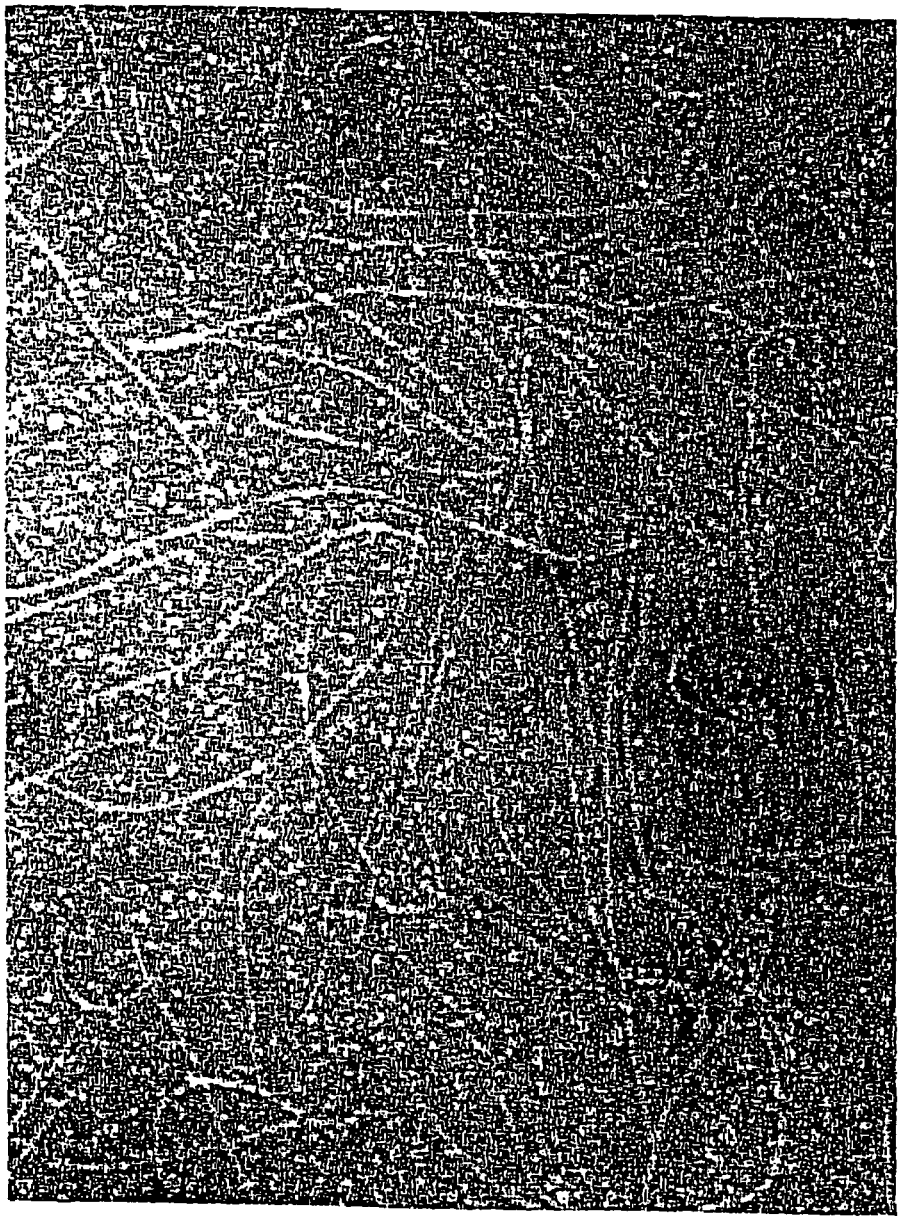
FIG. 5 is an electron micrograph of FtsZ protofilaments that form in the presence of GTP.
Figure 6:
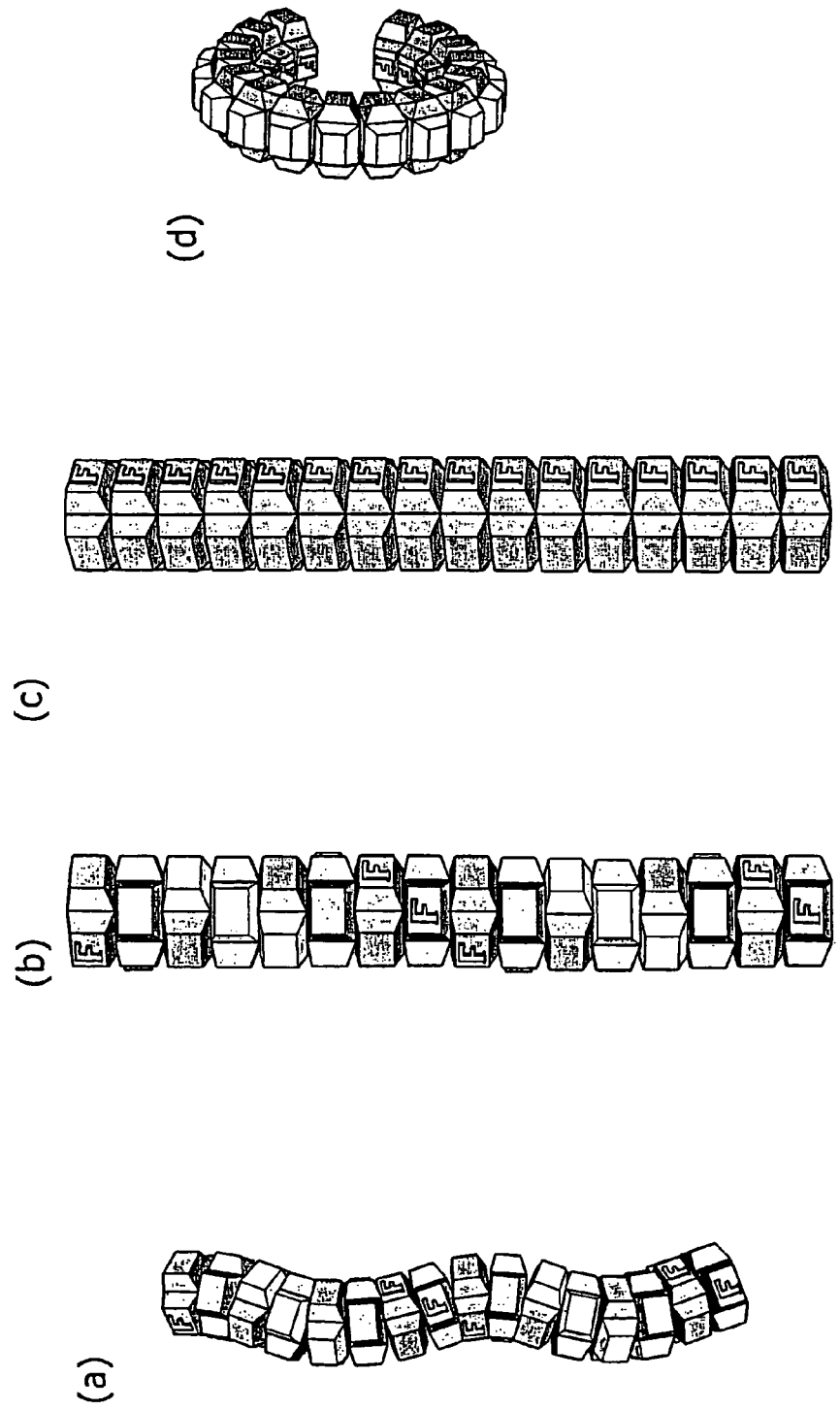
FIG. 6 is an illustration showing four possible arrangements of a linear protofilament assembled from identical subunits.

In vitro, FtsZ polymerizes in a guanine nucleotide-dependent manner into structures (protofilaments or protofilament bundles or sheets (see FIG. 5 and FIG. 6)) that are similar to tubulin polymers (microtubules). These activities, or more particularly, the inhibition or activation of these activities, may also be used to identify test compounds, such as peptide and small molecule compounds that are inhibitors or activators of FtsZ-mediated cell division.

The likelihood of prokaryotic cells developing resistance to molecules that inhibit FtsZ is relatively low for several reasons. First, FtsZ orthologs have a high degree of sequence conservation, especially in domains involved in GTP binding and hydrolysis, in subunit interaction required for polymerization, and in the interaction with proteins such as FtsA and ZipA. Second, as demonstrated herein and in the Examples, low, sub-stoichiometric levels of FtsZ inhibitors are likely to be sufficient to affect FtsZ function. Third, and most importantly, FtsZ is an essential, non-redundant protein, required for cell division. Use of FtsZ inhibitors may further provide an advantage when used in combination with other drug treatments in that it may provide a valuable time window for other drug treatments to have an effect by slowing down the rate of multiplication of the infectious organism.

In preferred embodiments, the present invention provides methods of identifying compounds and/or compound combinations that are inhibitors or activators of FtsZ activity. In related embodiments, the present invention provides methods of identifying compounds that are inhibitors or activators of proteins that interact with FtsZ, such as FtsA and ZipA.

Figure 7:
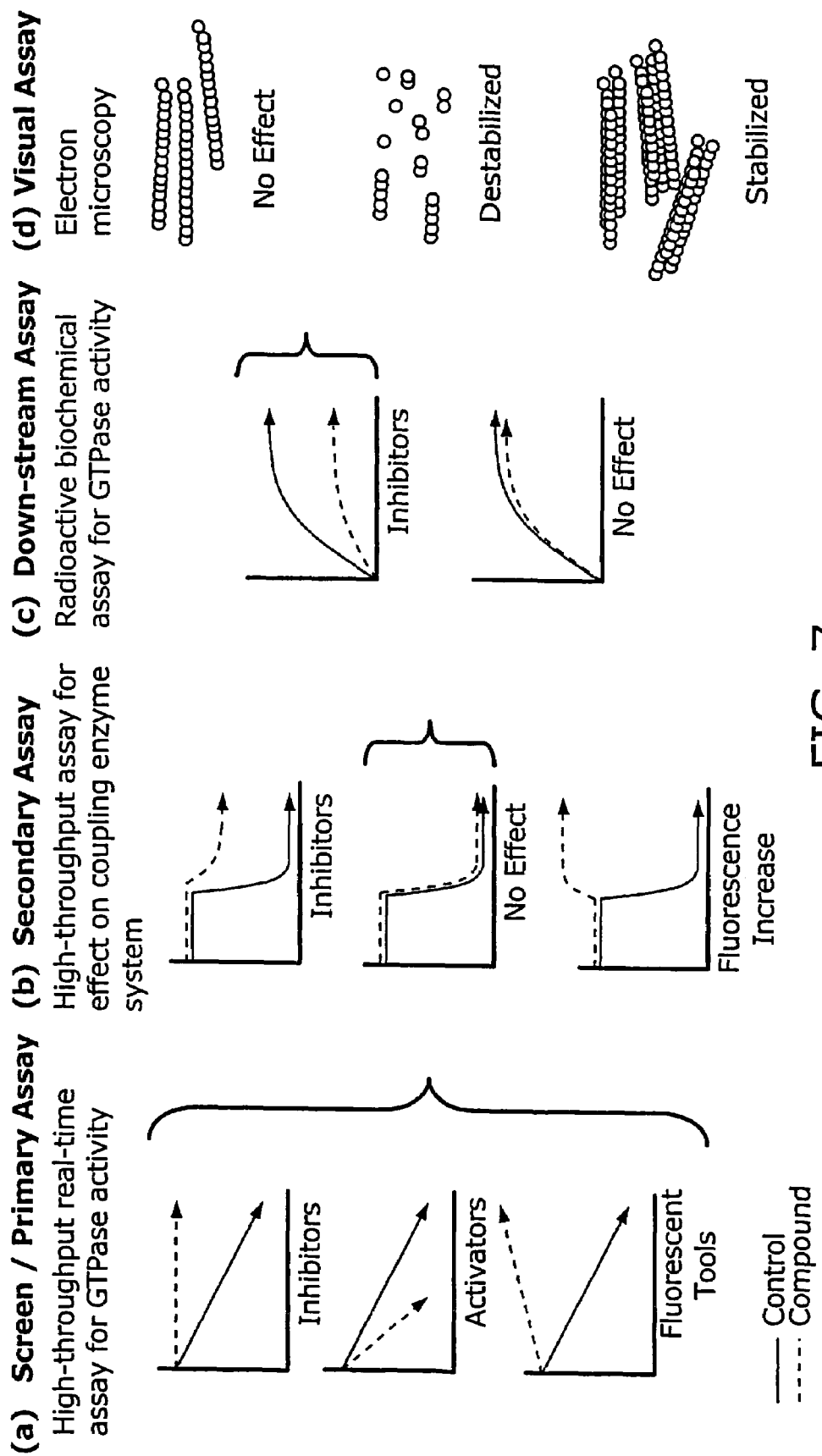
FIG. 7 is an illustration that depicts an overview of a screening process for identifying FtsZ inhibitors.

In related embodiments, the present invention provides assays for FtsZ activity that are based on cell morphology and FtsZ ring assembly in vivo in wild-type and ftsZ mutant cells. A visual assay may be used to determine the effect of a compound on polymerization, e.g., destabilizing or stabilizing polymerization (see FIG. 7, panel D). Other available assays include charcoal-based and thin-layer chromatographic assays for GTPase activity, negative-stain transmission electron microscopy to assess the activity of a compound on FtsZ polymers, and growth assays for assessing the anti-microbial activity of a compound. Such assays may include experiments that assess cell culture growth by, for example, culture turbidity in response to addition of compound.

For example, inhibition of FtsZ activity results in a block in the ability to form a cytokinetic ring structure, which results in abnormally long cells due to a decrease in septation without affecting cellular mass increase. An inhibition of FtsZ activity can be verified in vitro, e.g., by detecting a decrease in GTP-dependent polymerization of FtsZ and the concomitant GTPase activity see copending U.S. patent application Ser. No. 10/153,268, filed May 22, 2002. Alternatively, activation of FtsZ in vivo, or increased FtsZ abundance, results in hyper-formation of ring structures in the cell, which yields minicells due to polar septation. Similarly, an increase in in vitro polymerization-dependent GTPase activity may be observed in the presence of an FtsZ activator. It is noted that this increased GTPase activity may not necessarily result in increased polymer mass since the catastrophe rate may also increase.

The present specification describes an in vivo cellular assay that utilizes FtsZ wild-type and/or FtsZ-mutant microbial cells to screen compounds for anti-microbial activity. In certain preferred embodiments, a bacterial cell is provided that has, in addition to the mutation in FtsZ, a second mutation that affects the amount of drug that enters or remains in the cell, e.g., a mutation that affects an uptake or efflux pump, such as the multidrug efflux pump, or alters cell permeability, and may further include an expression vector encoding the FtsZ protein. Such cells may maintain a higher intracellular concentration of compound than wild type cells. It will be appreciated that expression of proteins in bacteria is standard in the art, as demonstrated below (see also Sambrook et al., *Molecular Cloning: A Laboratory Manual*, Cold Spring Harbor Press, N.Y., Ausubel et al., *Current Protocols in Molecular Biology*, Greene Publishing Associates, New York, V. 1&2, 1996, each of which is incorporated by reference herein).

Without limitation, the present invention encompasses the discovery that ftsZ mutants are, in some cases, significantly more sensitive to the adverse effect of a compound on its division ability at the permissive temperature relative to the congenic wild-type strain. In addition, the enhanced sensitivity is reversible, i.e., is reversed to equal that of the wild-type strain if a normal wild-type copy of the ftsZ gene is introduced into the ftsZ mutant cell on a plasmid. This suggests that the compound is either affecting FtsZ directly in vivo or a critical FtsZ-related step in the assembly of the division apparatus. In preferred embodiments, the present invention provides high throughput differential phenotypic screens using the wild-type parent and the congenic ftsZ84-ts mutant of *E. coli*. The rationale for such a screen is that some compounds in combination with the ftsZ mutation may cause enhanced lethality for the mutant at the permissive temperature, while the wild-type or congenic strain is used as a good control to examine the extent of filamentation and cytotoxicity induced by the compound.

In certain preferred embodiments differential phenotypic screens are carried out with wild-type and congenic ftsZ84-ts *E. coli* strains. This mutant is conditional-lethal because it grows and divides at 30° C., but undergoes a cell division block at 42° C. that leads to lethal cell filamentation. The division block of the ftsZ84 mutant at 42° C. is due to a drastic destabilization of the FtsZ ring (Z-ring) at high temperature (within a few minutes after the temperature shift up). The Z-ring is highly dynamic and is continually remodeled within a halftime of 30 seconds. In contrast the Z-ring in the ftsZ84 mutants displayed a 9-fold slower turnover at the permissive temperature. According to the present invention, the mutant Z-ring structure in ftsZ84 would be less robust than the wild-type ring at the permissive temperature of 30° C. and the inherent weakness of the mutant ring may be exacerbated in the presence of small molecules and other compounds that target FtsZ or the septal ring in vivo.

Those skilled in the art will appreciate that the in vivo screen can easily be extended to other conditional mutant alleles of ftsZ to conduct allele-specific screening of chemical libraries. In certain preferred embodiments, a putative mutation in a second gene that may interact with the conditional mutant allele, e.g., the ftsZ84-ts mutation, is substituted with a small molecule to elicit a phenotypic response, thus establishing a chemical genetic approach to identify small molecule modulators/antagonists of bacterial cell division. The hits obtained against different mutant alleles vis-à-vis the wild-type parent are compared to facilitate identification of chemical structures that show high affinity for targeting FtsZ or a FtsZ related step in cell division. Those skilled in the art will appreciate that this would be helpful in establishing downstream chemistry for the synthesis of structural analogs to perform SAR studies.

In preferred embodiments, the in vivo screen described herein is conducted with other conditional-lethal mutations in cell division genes such as ftsA, ftsI, ftsQ ftsK etc. or with mutations in new, as yet unidentified, division genes in eubacteria. There are multiple temperature-sensitive alleles available in a number of known fts genes for allele-specific screening as well. The present in vivo screens provide advantages over other cell division screens in their rapidity, simplicity, and cost effectiveness, as well as the specificity for the process being targeted, namely cell division in bacteria. In addition to *E. coli* as the organism being used for screening, the inventive in vivo screen can be carried out with conditional cell division mutants in other model or pathogenic bacteria such as *Vibrio cholerae* (Gram-negative), *Staphylococcus aureus* (Gram-positive), *Shigella flexneri* (Gram-negative), *Bacillus subtilis* (Gram-positive), etc.

The species listed above may further provide models for broad spectrum testing of the likely effect of compounds on other species. For example, FtsZ is subject to temporal, spatial, and developmental regulation in *B. subtilis*. During exponential growth, Z-rings form exclusively at midcell as a prelude to binary fission in a manner similar to that in *E. coli*. At the onset of sporulation in *E. coli*, FtsZ shifts from a medial to a bipolar pattern of localization, forming a Z-ring near each pole of the cell. Subsequently, one Z-ring matures into the sporulation septum, while the other Z-ring is dissipated. A similar Z-ring switching mechanism is expected to be operative in *B. anthracis* during spore formation. Therefore, FtsZ inhibitors could also be very useful tools to prevent anthrax spore formation, because asymmetric Z-ring assembly near one pole is a critical prerequisite for successful sporulation in *B. subtilis*.

In yet other preferred embodiments, sensitized strains carrying mutations in regulatory genes that affect the level or the stability of key cell division proteins are used in the inventive in vivo assay. For example, such regulatory mutations may reside in transcription factors or in proteolytic enzymes. Small molecules can be identified that may either alleviate or worsen the sensitized state of cell division in such bacterial strains.

In one particularly preferred embodiment, both the wild-type and the conditional mutation, e.g., ftsZ84-ts mutant, carry a null mutation in the major drug efflux pump, AcrAB, in E. coli. This prevents or reduces efflux of certain of the putative hits from the cell. The ftsZ84-ts mutation renders the strain temperature-sensitive by destabilizing the division machinery at the non-permissive temperature of 42° C., yielding long filamentous cells. However, at the permissive temperature of 30° C., the temperature-sensitive cells grow like wild-type and are rod-shaped. Thus, the present invention provides assays that detect the phenotype of wild-type and mutant bacterial cells (e.g., the congenic thermosensitive ftsZ84 E. coli mutant DRC13 and their derivatives, which lack the major multidrug efflux pump AcrAB) in the presence and absence of compound.

In preferred embodiments, the present invention provides assays including the steps of 1) expressing the FtsZ protein in a wild-type cell, 2) contacting the cell with a compound, and 3) detecting a defect in cell division. For example, the defect in cell division may be an activation of cell division, e.g., caused by excessive FtsZ ring assembly. This would result in a phenotype of excessively short cells without DNA, called minicells, resulting from division activity at the cell poles. In addition, under conditions of excessive intracellular polymerization of the FtsZ protein, the FtsZ rings would persist longer and more stably, thereby impeding ring constriction essential for septation. Alternatively, the defect in cell division may be an inhibition of cell division, e.g., caused by a blockage to intracellular polymerization of the FtsZ protein or hyperstabilization of the FtsZ polymers This block in FtsZ activity may result is long filamentous cells that divide infrequently or completely fail to divide.

Figure 8:
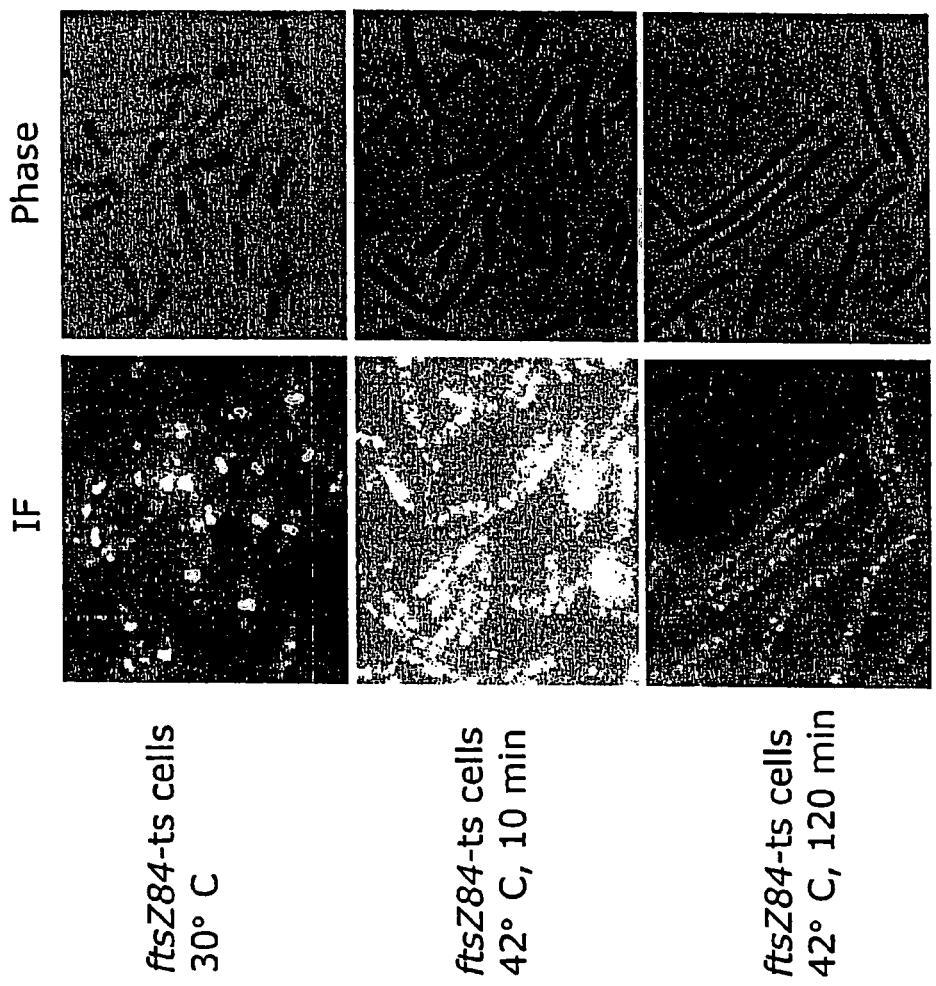
FIG. 8 shows photographs of immunofluorescent staining and phase contrast microscopy of ftsZ84 mutant cells with thermolabile FtsZ84 rings.

In another embodiment, the compound is used in an assay that determines its ability to decrease or exacerbate an ftsZ phenotype. In certain preferred embodiments, the invention provides a method of identifying compounds that affect cell division, comprising steps of contacting a cell that is defective in cell division (e.g., ftsZ84 cells having a thermosensitive mutation in the gene encoding FtsZ and a signature sequence of SGGTGTG) [SEQ ID NO: 3]) with a compound of interest; and detecting an alteration in the phenotype of the cell. More particularly, the method involves the steps of 1) contacting an ftsZ cell with a compound of interest, and 2) detecting an alteration in the phenotype of the ftsZ cell (e.g., a destabilization in the Z ring structure). Typically such ftsZ cells are temperature sensitive ftsZ cells, e.g., ftsZ84 cell that grow and divide at 30° C. and undergo a division block at 42° C. due to a destabilization of the Z-rings at high temperature (see FIG. 8). ftsZ84 cells display approximately 9-10-fold reduced FtsZ GTP binding and GTPase activities compared to wild-type cells. ftsZ84 cells lacking the multidrug efflux pump AcrAB would have a decreased ability to expel compound from the cell, thus allowing increased concentrations of a compound to accumulate in the cell potentially resulting in an exacerbated phenotype caused by the compound in that cell at the permissive temperature of 30° C. A phenotype detected at 30° C. in the presence of a compound that inhibits FtsZ activity would be mimicking the failure to form Z rings in the ftsZ84-ts cells at 42° C. (a phenotype akin to the synthetic lethal interactions between two genetic mutations).

Another assay system provided by the present invention that may be utilized to identify compounds that affect cell division includes a bacterial cell that has a mutation affecting a multidrug efflux pump and further contains an expression construct encoding the ZipA protein. As noted above, the bacterial cell strain ftsZ84 is an example of a cell that has a mutation affecting a multidrug efflux pump. In addition, as noted herein, the ZipA protein stabilizes intracellular assembly of the FtsZ ring. It has been shown that ftsZ84 cells expressing increased concentrations of ZipA, e.g., via introduction of a second copy of a ZipA gene into the cell, have decreased thermosensitivity at the restrictive temperature of 42° C.

In related embodiments, the present invention provides a method of utilizing the ftsZ84 strain in combination with a multidrug efflux pump mutation and a second copy of ZipA, described above, to identify a compound that affects cell division, or alternatively a method of validating whether a compound affects cell division. The method involves observing the effect of the compound on the phenotype of ftsZ84 cells expressing increased concentrations of ZipA (see U.S. Pat. No. 5,948,889, incorporated by reference herein). Compounds that are inhibitors will diminish the suppression of the thermosensitivity of the ZipA expressing ftsZ84 cells at increased temperatures, resulting in a destabilization in the ring structure. Alternatively, a second copy of ZipA may increase the stability of the FtsZ ring in ftsZ84 cells and may thereby alleviate the lethality of FtsZ compounds.

A key step in bacterial cell division is the assembly of the septal ring organelle at the division site that guides the circumferential syntheses of cell wall and membrane for biogenesis of the division septum. The septal ring is assembled by the ordered recruitment of eight essential division proteins to the FtsZ ring scaffold in E. coli (see FIG. 4). It is therefore likely that the inventive in vivo screen can identify small molecules that target the protein-protein interaction interfaces between FtsZ and other division components in the septal ring and not the FtsZ protein per se, as well as identifying molecules that target FtsZ. Those skilled in the art would appreciate that such molecules are highly desirable as lead compounds for antibacterial drugs. The probability of spontaneous resistance arising against such drugs would be low as they target the area of interaction between two proteins and key amino acid residues contributed by both proteins for such interaction may need to be mutated for resistance to develop.

Using defined cell division mutants in the inventive in vivo screens increases the specificity of the screening process and allows compounds to be identified rather easily, which may disrupt one or the other of multiple protein-protein interactions that occur in the septal ring complex. As described herein, the screening can be done with any bacterial organism carrying cell division mutations, thus providing facile method to screen against division genes that may be present in one organism and not the other. The in vivo screen described above differs other in vivo screens such as the yeast two-hybrid screen in that the bacterial cell itself, and not yeast, is being used to screen for molecules that target a complex process such as cell division in bacterial cells.

According to the present invention, the hits obtained from the in vivo screens can be validated by growth and phenotype assays against a wide range of bacteria and by a range of in vitro biochemical assays to pinpoint the target of their actions, whether for example the target is FtsZ or the interaction between FtsZ and another essential division protein. The hits obtained from the in vivo screen can also be further characterized phenotypically, e.g., using electron microscopy to observe effects on protofilament formation. One useful in vitro assay system is the charcoal-based GTPase assay described by Lee et al. *J. Biol. Chem.* 267:1212-1218 (1992), incorporated herein by reference. Another assay is the malachite green-phosphomolybdate assay (Akiyama, Y., Kihara, A., Tokuda, H. and Ito, K. 1996, J. Biol. Chem. 271:31196-31201, incorporated herein by reference (see FIG. 9)). Yet another assay includes negative-strain transmission electron microscopy of FtsZ polymers. Another in vitro assay includes right-angle light scattering. More traditional anti-microbial screening assays are described by de Boer et al. in U.S. Pat. No. 5,948,889 (col. 8-9), incorporated herein by reference.

It will be appreciated that the in vivo assay of the present invention may be used to validate any compounds identified by in vitro assays. Other in vivo assays may also be used for validation. For example, the effect on FtsZ ring assembly in live cells carrying an ftsZ mutation may be assessed. Alternatively, the effect on FtsZ ring dynamics in live cells using fluorescence photobleaching recovery assays may be assessed. The effect on protein-protein interactions between FtsZ and other essential division proteins, such as FtsA or Zip A may be assessed by methods standard in the art, e.g., antibody pull down assays and/or co-sedimentation assays.

It will be appreciated that any compound may be tested in the inventive in vivo assay system described herein to detect activators or inhibitors of cell division. It will also be appreciated that such compounds may be generated by any art available means. For example, certain compounds of the galanthamine library, described in U.S. patent application Ser. No. 09/863,141, incorporated herein by reference in its entirety, have been screened. In addition, marine extracts (e.g., available from National Cancer Institute (NCI)) can be screened for FtsZ inhibiting or activating activity in vivo. The NCI extracts contain a mixture of about 10-12 compounds. If an extract scored positive in the in vivo assay of the invention, the extract would be separated into its constituent components and rescreened to identify the active component(s).

Figure 23A:
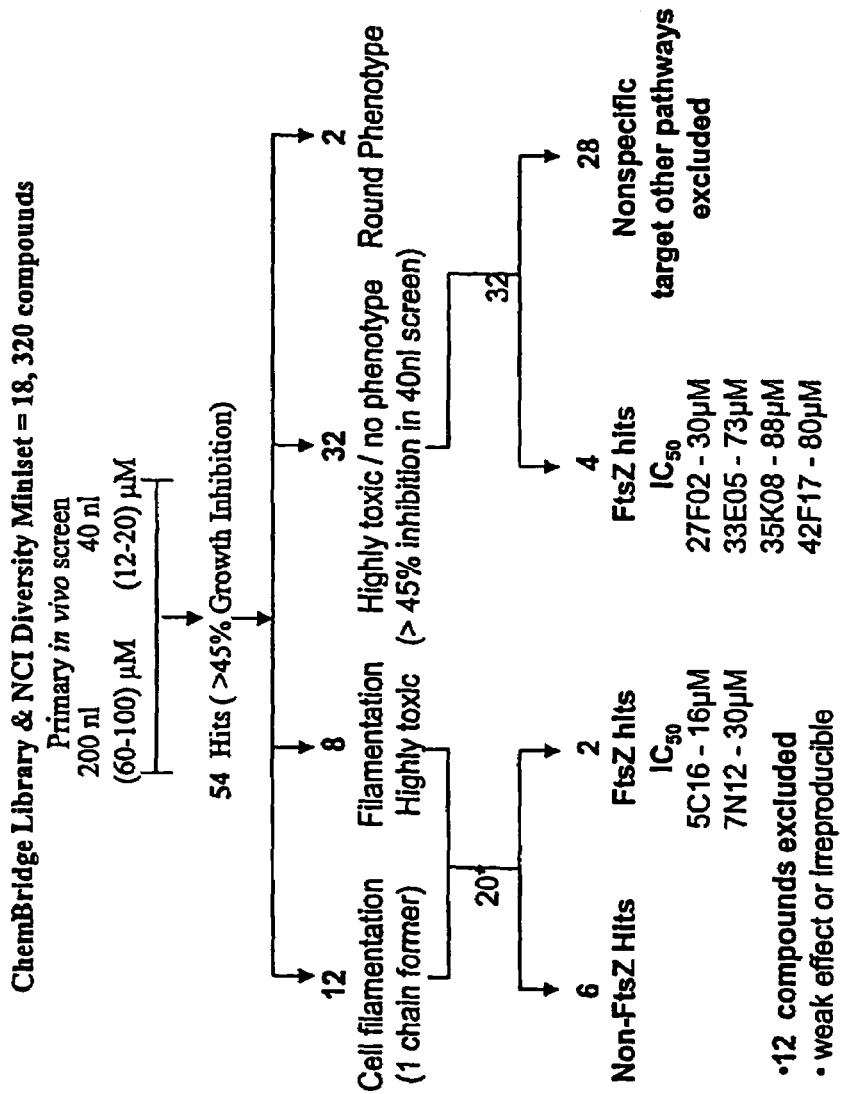
FIG. 23 is a flow chart that depicts results obtained in the in vivo screen that was used to identify inhibitors of bacterial cell division.

As described in Example 1, an in vivo screen for molecules that inhibit bacterial cell growth by perturbing the cell division process was performed. A total of 18,320 compounds, including the 16,320 member Chembridge DiversetE Library and 2000 member NCI Diversity Set, were screened against two congenic strains of *E. coli* that both lack the major drug-efflux pump AcrAB, yet differ by a point mutation in the ftsZ gene. Compounds that inhibit bacterial division in the sensitized ftsZ mutant strain (the terminal phenotype of filamentation that could eventually lead to cell death), but do not exhibit such pronounced effect in the wild-type strain, were expected to target either the mutant FtsZ or the protein-protein interaction interface between FtsZ and other components of the cell-division machinery. Compounds that inhibited greater than or equal to 45% of cell growth were identified as positive hits. From the two libraries, a total of 172 hits were identified on an ftsZ-ts mutant, ftsZ84. A filamentation defect was observed for 52 of these compounds, and cell lysis or change in cell shape was observed for the remaining 121 (see FIG. 10). Additional compounds were identified on wild-type *E. coli* cells (see FIG. 10). FIG. 23 is a flow chart that depicts results obtained in the in vivo screen, and FIG. 16 illustrates the chemical structure of various cell division inhibitors identified using the screen.

The analysis of the in vivo screening results revealed the following categories of compounds: 1) compounds that inhibited growth in both the wild-type and the congenic ftsZ84-ts mutant strains; 2) compounds that inhibited growth only in the wild-type strain; and 3) compounds that inhibited growth only in the congenic ftsZ84-ts mutant. Regarding the category 2 compounds, the lack of any visible adverse effect on the ftsZ84-ts mutant raises the possibility that one or a subset of these compounds may stabilize the mutant FtsZ84 ring. The increased stability of the wild-type FtsZ ring in the presence of such compounds might retard the constriction of the septal ring and this would result in a defect in septum synthesis with consequent filamentation in the wild-type strain. One skilled in the art could easily test whether the category 2 compounds actually suppress the temperature-sensitive growth of the ftsZ84-ts mutant at the non-permissive temperature of 42° C.

Figure 17:
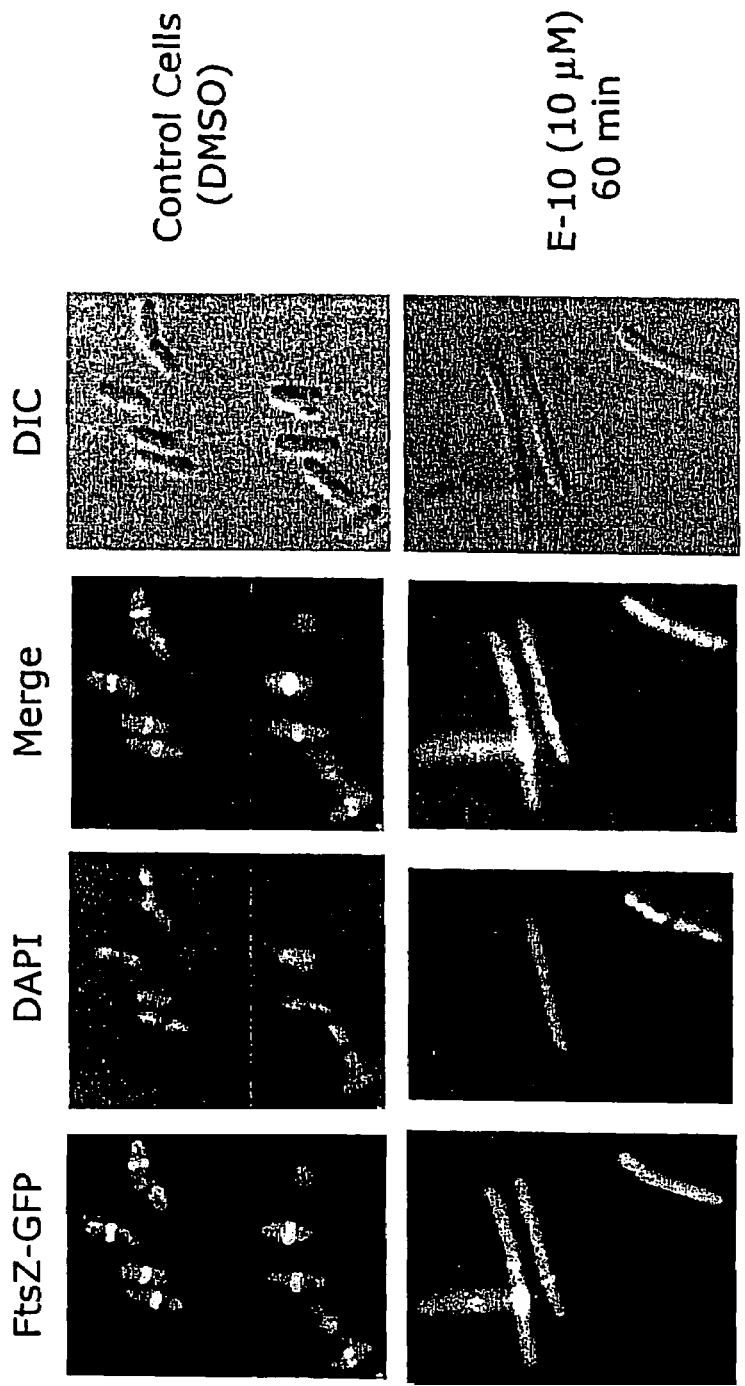
FIG. 17 shows images that illustrate the effect of compound 26E-10 on FtsZ ring assembly in *E. coli*.

Compound, 26E-10, which was identified in the in vivo cell based assay, was extensively investigated using various in vivo assays (Examples 1, 3). The structure of 26E-10 is depicted in FIG. 16, and its effects on FtzZ ring assembly in *E. coli* are depicted in FIGS. 17 and 18.

The compounds identified using the in vivo assay expanded the repertoire of cell division inhibitors that had been initially identified using preliminary in vitro screening of the two libraries (see Example 2). Five in vitro inhibitors were identified and verified in various in vitro assays and also using in vivo assays for bacterial growth and/or for their effects on the formation of the FtsZ ring structure in the cell. Assays used included, e.g., a TLC assay, a GTPase assay using activated charcoal, a polymer sedimentation assay, negative-stain electron microscopy, or a polymerization assay using fluorescent tubulin, each of which are known in the art. The five inhibitors are 58P-18, 16L-09, 18M-04, 27D-12, and 27F-02, which are depicted in FIG. 11. Of these compounds, 27D-12 is the most cell-permeable, is effective against gram positive bacteria at very low concentrations and also kills gram negative species; 18M-04 is relatively impermeable with respect to most gram negative bacteria tested but kills gram positives. 27D-12, 27F-02, and 18M-04 are destabilizers of FtsZ protofilament assembly in vitro, while 16L-09 is a stabilizer of FtsZ protofilament assembly in vitro. 58P-18 is a modest FtsZ protofilament stabilizer in vitro but induces a cell division inhibitory phenotype in *E. coli* after prolonged treatment.

Figure 12:
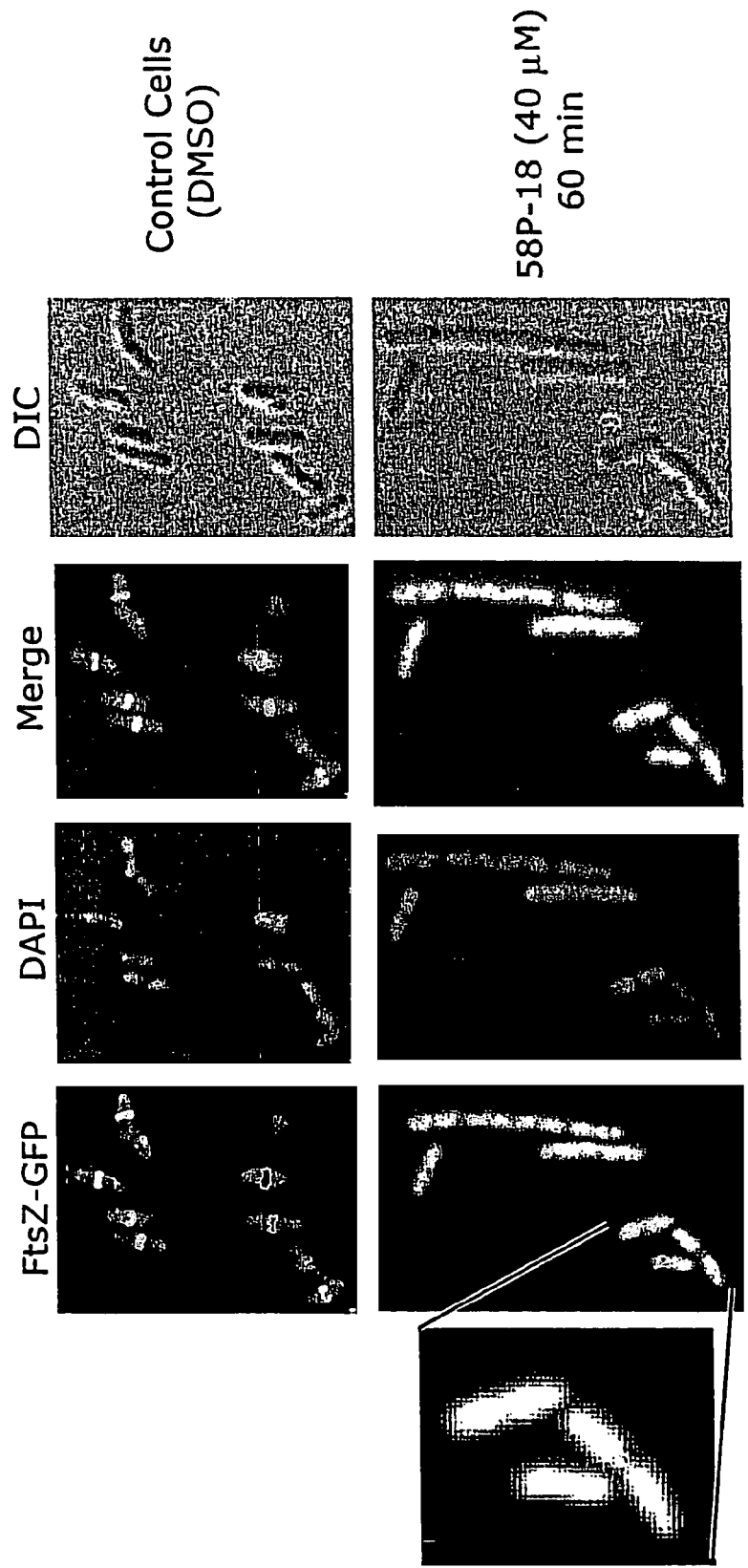
FIG. 12 shows images of *E. coli* cells that contain an AcrAB mutation and express an FtsZ-GFP fusion protein that have been treated with the compound 58P-18.
Figure 13:
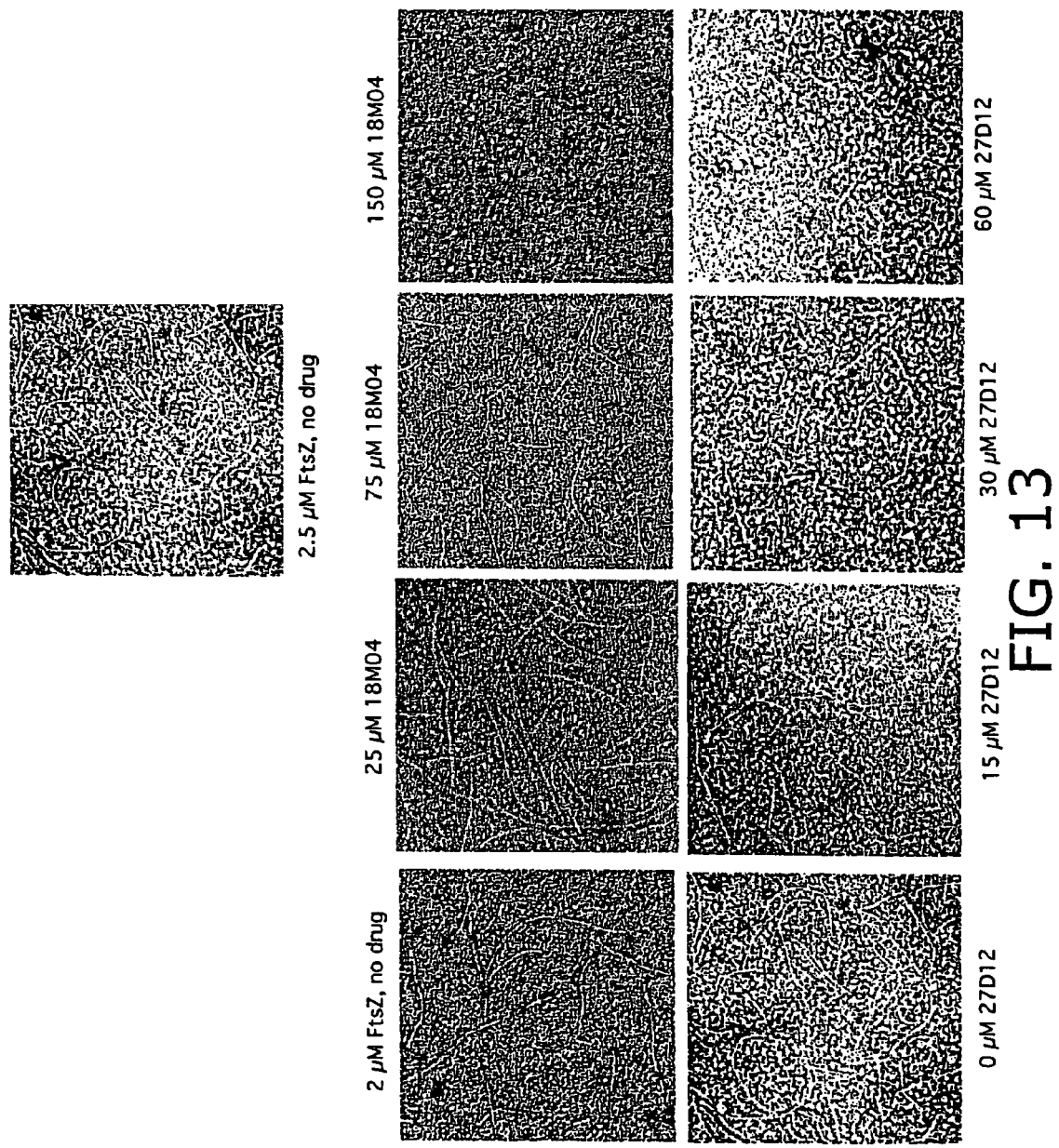
FIG. 13 is an electron micrograph image of the effect of compounds 18M-04 and 27D-12, which destabilize FtsZ polymers in a dose dependent manner.
Figure 14:
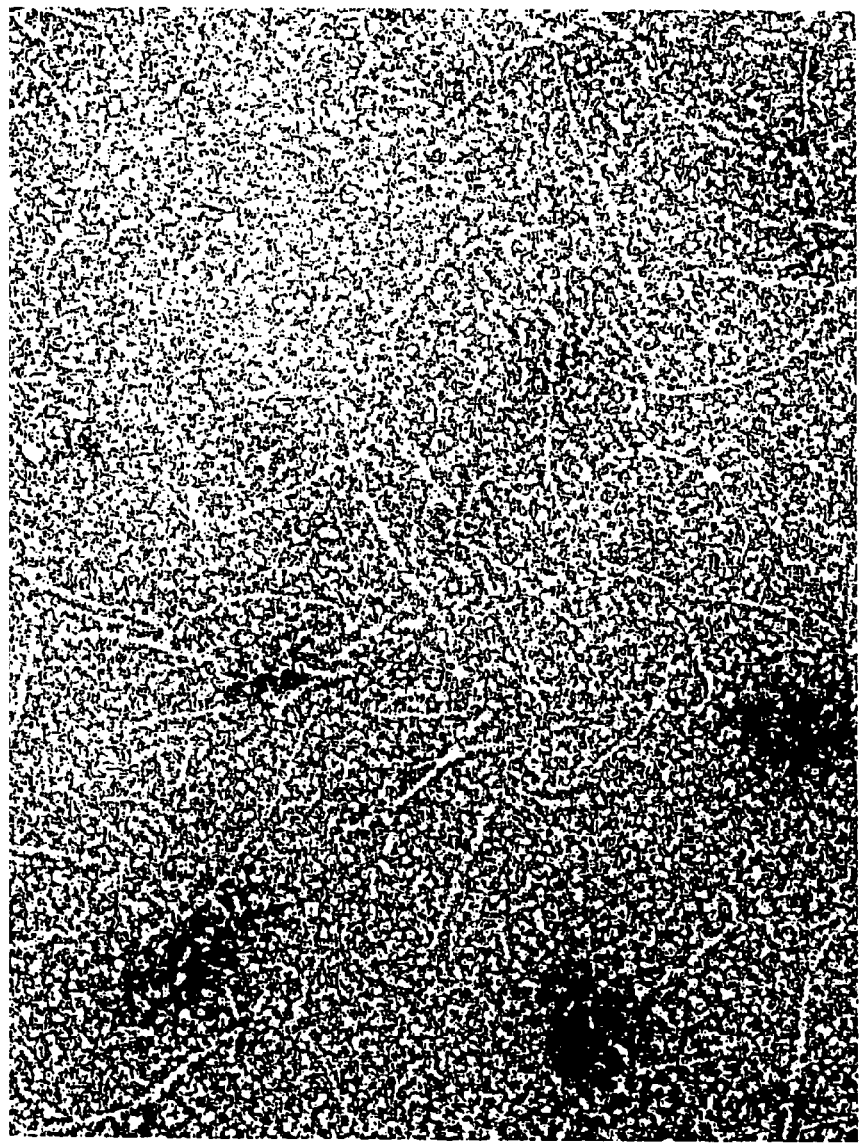
FIG. 14 is an electron micrograph of protofilaments in the presence of compound 27D-12.
Figure 15:
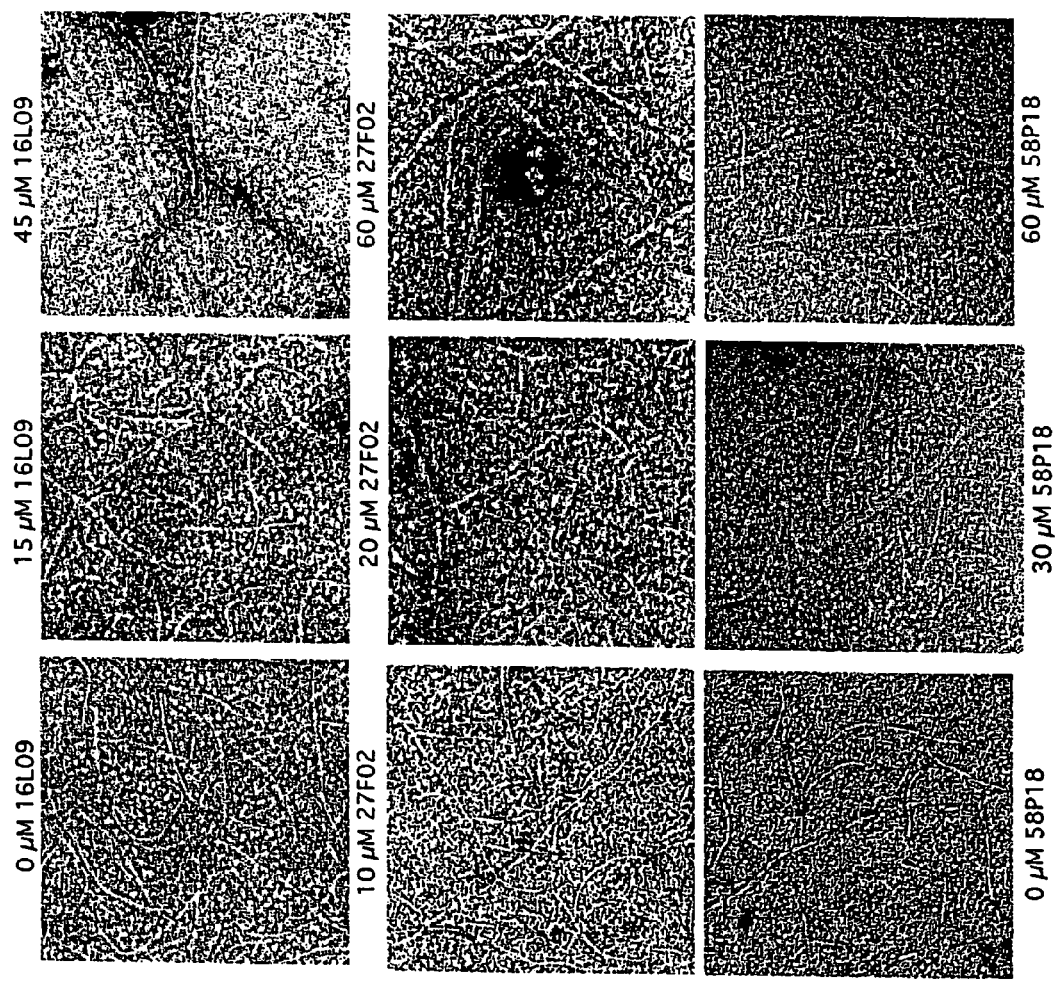
FIG. 15 is an electron micrograph image of the effect of compounds 16L-09, 27F-02, and 58P-18, which cause pairing and/or bundling of FtsZ protofilaments.

These five compounds can thus be divided into two classes. The first class includes the compounds 18M-04 and 27D-12, which have a dose dependent destabilizing effect on the polymers (see FIG. 13 and FIG. 14). The second class of compounds includes 16L-09, 27F-02, and 58P-18, which cause bundling of FtsZ protofilaments (mostly via pairing of protofilaments) that could alter the FtsZ ring dynamics in vivo (FIGS. 12 and 15).

The minimum inhibitory concentrations for some of the identified compounds against various bacterial species and strains were evaluated and results are shown herein (see, e.g., FIG. 19 for MIC values of compounds identified using in vitro assays, and see Table 3 for MIC values for compound 26E-10). The data demonstrate that some of the compounds identified by the inventive assays kill a wide range of bacteria at concentrations between 2 and 40 µM.

Two compounds, 26E-10 and 58-P18, appeared to affect cell division by targeting FtsZ ring formation in vivo. The compound 26E-10 has a strong in vivo phenotype, as demonstrated below. Moreover, 58P-18 shows both in vitro GTPase FtsZ inhibition and an in vivo phenotype.

While all of the compounds identified and verified using the in vitro GTPase activity based screens necessarily exhibit an inhibitory effect on FtsZ GTPase activity, only a subset of the compounds identified using the in vivo assay exhibited such an effect when tested in vitro. Such compounds may either target an aspect of FtsZ activity that is not reflected in its in vitro GTPase activity, may target another molecule involved in cell division, may disrupt interactions between two or more molecules, etc.

Mutant Strains

In preferred embodiments, strains other than acrAB are generated to contain ftsZ mutations for screening for FtsZ interactive compounds in vivo. In certain preferred embodiments, the inventive in vivo assay may be conducted with strains carrying a mutation in the tolC gene that encodes a channel-tunnel protein linking the inner and the outer membrane in E. coli. The tolC mutation is known to enhance the permeability of cells to a variety of molecules. In other preferred embodiments, both the acrAB and tolC mutations can be combined as this is known to confer maximum permeability to E. coli. After identifying compounds that affect cell division, the molecules can be tested for their cell permeability in an E. coli strain that is wild-type for acrAB and tolC genes. If some of the hits prove impermeable, downstream chemistry can be employed to enhance their cell permeability.

In certain preferred embodiments, the screen is carried out using ftsI-ts mutants. The ftsI gene codes for the penicillin-binding protein 3 (PBP 3) in E. coli and is essential for the synthesis of septal cell wall in eubacteria. PBP 3 is the only one out of eight PBPs characterized in E. coli dedicated to septum synthesis and cell division. The rest of the PBPs are involved in cell wall synthesis along the long axis of the cell and presumably do not participate in cell division. As is well known, the PBPs are the lethal targets of penicillin and its derivatives, as well as cephalosporins (the beta-lactam class of antibiotics). The beta-lactams covalently acylate the active site serine residue of PBPs, which are generally bifunctional enzymes carrying out both transglycosylation and transpeptidation activities essential for cell wall synthesis. PBP 3, however, is believed to be a monofunctional transpeptidase. To date, no allosteric inhibitor outside the active site of PBPs has been described.

In vivo screens using ftsI-ts strains have the potential to identify molecules that may either allosterically affect PBP 3 function or disrupt protein-protein interactions between PBP 3 and other cell division proteins. An allosteric PBP 3 inhibitor could be a useful starting point to design or screen for such allosteric inhibitors against other PBPs that are involved in the essential and delicate process of cell wall elongation and in the maintenance of the osmotic integrity of the eubacterial cell.

Other embodiments of the invention provide a novel thermosensitive ftsZ mutation, designated ftsZ26, for use in the in vivo screen that consists of a 6-codon insertion near the 5'-end of the gene. This mutation, like the ftsZ84 mutation, causes morphological changes in E. coli even at the permissive temperature. The changes include cells with blunt poles and carrying protrusions to one side, Y-shaped cells, and minicells. The altered polar morphology is a result of cell division and is due to the aberrant geometry of FtsZ rings that assembled non-perpendicular to the long axis of the cell. Upon shift to the non-permissive temperature, ftsZ26 cells form filaments that are morphologically similar to the filaments formed by the ftsZ84 mutant, except for the poles that form at 30° C. The thermosensitivity and the altered geometry of ftsZ26 rings argue that FtsZ-specific small molecules may likely exacerbate the assembly defect of ftsZ26 under permissive conditions, thus rendering this mutant amenable for use in the inventive high throughput whole-cell screens. In certain preferred embodiments, the acrAB deletion is introduced into both ftsZ26 and its congenic parent for screening purposes.

In other preferred embodiments, a strain in which expression of ftsZ is kept at a low level sufficient for viability and subject to modulation by an inducer is provided. The chromosomal ftsZ copy is rendered non-functional in the presence of a plasmid that expresses the essential ftsZ gene from of an inducible, ectopic promoter. A frame-shifted allele of ftsZ, e.g., obtained by cutting and filling-in the unique EcoRI site in ftsZ, is available in the art. This allele is designated ftsZ$^O$. This mutation is introduced into the strain background DRC39 (MC1000 ΔacrAB::Kan) by P1 transduction with the closely linked leu::Tn10 marker. Before transducing the null ftsZ$^O$ allele, a plasmid is introduced into DRC39 that contains the wild-type ftsZ under the control of arabinose(Ara)-inducible pBAD promoter. The transductants are plated on LB plates containing Ara (a range of Ara concentrations are tested) to maintain viability) and the transductants are screened on glucose plates to look for cell death in the absence of ftsZ expression from pBAD. This would confirm the presence of the ftsZ$^O$ allele in the chromosome.

After obtaining the desired low expression ftsZ strains, growth and viability assays are carried out at different Ara concentrations to identify the minimum inducer concentration sufficient for maintaining cell viability. Screening is performed at this low inducer concentration to make the strain hypersusceptible to FtsZ specific small molecule hits.

As mentioned above, many species of microorganisms have conserved FtsZ and thus may be used in the in vivo screen of the invention. One of these species is B. subtilis, and another is B. cereus. These gram-positive bacteria may be used as surrogates for the closely related pathogen B. anthracis, the causative agent of anthrax, because cell division is an essential, conserved cellular process. A temperature-sensitive allele of ftsZ has been described in B. subtilis in which the only copy of ftsZ is fused to wild-type green fluorescent protein (GFP) (strain designated PL642). Since wild-type GFP is prone to misfolding at higher temperatures (37° C. and above), the defect in PL642 is likely due to misfolding of the entire fusion protein at the high temperature such that cells are viable at 30° C. but unable to form colonies between 42-45° C. Thus, according to the present invention, PL642 can be easily adopted for the in vivo screens of the invention.

For screening against E. coli, standing growth of 40-μl cultures in 384-well plates at 30° C. is suitable. B. subtilis and B. cereus are aerobic organisms and are typically cultured with vigorous aeration for vegetative growth to avoid sporulation. However, these bacteria can also grow anaerobically or in the presence of low oxygen. If $KNO_2$ (potassium nitrite), which acts as an electron acceptor, is added, it is possible to grow B. subtilis or B. cereus in stationary cultures, e.g., in microtitre plates or in other conditions in which the $O_2$ concentration is low. Of course other culture systems, in which $O_2$ is provided, e.g., by aeration, can also be used.

As demonstrated herein, the in vitro FtsZ hits as well as the in vivo hit 26E-10 efficiently killed B. subtilis and B. cereus. This demonstrates first that E. coli screens can identify broad-spectrum compounds that would be lethal for B. anthracis and other biothreat bacterial agents. Furthermore, using E. coli as a model organism in whole-cell screens allows us to exploit the well-characterized division mutants and to circumvent the need for a BL3 facility required for handling virulent pathogens. According to the invention, compounds may be screened directly in other bacterial species typically utilized in the laboratory, such as B. subtilis and B. cereus. Alternately, compounds may be screened directly in pathogenic species or strains.

Compound Combinations Exhibiting Enhanced Inhibitory Effects

As described elsewhere herein and in copending applications U.S. Ser. Nos. 09/863,141; 10/153,268; and 10/180,348 the in vitro and in vivo screens resulted in identification of a number of compounds that inhibit cell division, many of which also affect FtsZ GTPase activity as measured using in vitro assays. In addition, a number of compounds screened using the inventive in vivo assay induced cell filamentation and death without apparently affecting FtsZ GTPase activity in any significant way at the concentrations tested. For example, such compounds may have no detectable effect, or an insignificant effect (e.g., less than 1% inhibition, or less than 5% inhibition), at concentrations up to 20 $\mu$M, 50 $\mu$M, 100 $\mu$M, or even higher.

Thus it was determined that many of the compounds showing in vivo effects do not affect FtsZ GTPase activity and/or protofilament assembly in vitro. These compounds may target other proteins involved in cell division, e.g., other proteins in the septal ring. In general, the compounds may act by inhibiting expression, activity, processing, etc., of any of the proteins involved in the cell division process. The compounds may target protein-protein interactions between FtsZ and other essential septal ring components, rather than FtsZ per se. Without wishing to be bound by any theory, molecules that disrupt protein-protein interactions are highly desirable because the probability of resistance developing against them is low. Alternatively, these compounds may cause cell filamentation by activating a checkpoint, such as the SOS-inducible division inhibitor SulA, that blocks Z-ring assembly. Another possibility is that these compounds induce the MinC division inhibitor to be activated to block cell division, The inventors recognized that particular combinations of inhibitors might result in enhanced efficacy relative to the individual compounds, particularly in view of the fact that the identified inhibitors appear to act via a diverse set of targets and/or mechanisms. The inventors hypothesized that sub-lethal (i.e., below the MIC) concentrations of these compounds, when present in combination, would result in a phenomenon resembling the concept known in the field of genetics as "synthetic lethality". As is known to one of ordinary skill in the art, synthetic lethality may occur when an organism harbors two mutations, neither of which by itself is enough to result in a lethal phenotype, but which, in combination, do result in a lethal phenotype. For example, certain mutations confer temperature sensitivity on an organism, such that the organism cannot live at elevated temperature if it harbors the mutation but can survive at the permissive temperature. Two such mutations (typically in different genes) are said to exhibit "synthetic lethality" if an organism harboring both mutations is now unable to survive even at the permissive temperature.

In the context of administering inhibitory compounds, the inventors hypothesized that a similar phenomenon might occur, i.e., concentrations of compounds that were too low to result in significant inhibition of cell survival and/or division might, when present in combination, result in such inhibition. In order to determine whether this would indeed be the case, the inventors administered a variety of different compound combinations to cells growing in culture, as described in Example 5. In particular, six different FtsZ GTPase activity inhibitors were administered in binary combination with either of two cell growth inhibitors that do not apparently inhibit FtsZ GTPase activity. In other words, two different cell growth inhibitors that do not apparently inhibit FtsZ activity were used in various combinations with one of the FtsZ inhibitors. Thus each combination included one FtsZ GTPase activity inhibitor and one inhibitor of cell division that does not apparently inhibit FtsZ GTPase activity. Only a subset of the potential two-compound combinations were tested, but results may readily be extended to other combinations and to other compounds not yet tested in combination.

The compounds were used in combinations in which each compound was present at a concentration lower than its MIC. The concentrations were such that cells were able to grow without any significant perturbation in culture densities in the presence of an individual inhibitor. The results showed that each of 5 FtsZ GTPase activity inhibitors (out of 6 compounds that inhibit FtsZ GTPase activity), in combination with a cell growth inhibitor that apparently does not affect FtsZ GTPase activity, prevents or inhibits cell survival (i.e., kills cells) or proliferation at concentrations of each inhibitor that are significantly lower than their individual MICs. These results support the concept that combination therapy using cell division inhibitors at concentrations lower than their individual MICs is likely to have significant advantages. In addition, a combination of two FtsZ GTPase activity inhibitors at sub-MIC concentrations of each inhibitor also exhibited synergistic growth inhibition, although the level of synergism appeared to be less than typical amounts when a FtsZ GTPase inhibitor and a cell division inhibitor that does not appear to inhibit FtsZ GTPase activity were applied in combination. Thus the results support combination therapy in which a FtsZ GTPase activity inhibitor and second inhibitor of cell division that does not inhibit FtsZ GTPase activity are administered at sub-MIC concentrations and also combination therapy in which two FtsZ GTPase activity inhibitors are administered at sub-MIC concentrations.

Since molecules that do not directly affect FtsZ (e.g., molecules that do not affect FtsZ GTPase activity and/or assembly) are likely to target different septation proteins in the cell division pathway, the present invention provides methods of using these molecules in combination to kill bacterial or other microbial cells. According to the non-limiting theory of the present invention, two or more molecules can be applied to a single cell simultaneously to affect cell growth and division at multiple points resulting in the inhibition of cell division or cell growth. Because the septal ring is critical for bacterial division and is a dynamic structure, without limiting the theory of the invention, we propose that simultaneous partial inhibition of two or more essential proteins residing in the septal ring can lead to inhibition of cell division and cell growth. Similarly, partial inhibition of two or more non-structural proteins (i.e., proteins that do not form part of the septal ring) involved in cell division, or partial inhibition of one or more proteins residing in the septal ring and one or more non-structural proteins involved in cell division can also lead to inhibition of cell division and cell growth. Of course combinations of compounds that both target a single protein, e.g., FtsZ, can also be used. Such compounds may, but need not, target different sites within the protein. It is expected that the compound combinations will inhibit cell division, as the compounds do when applied individually. However, it is possible that a plurality of compounds, each of which inhibits cell division when used alone may, when used in combination, affect cell survival and/or proliferation by means other than inhibiting the cell division process.

There are several advantages to using combinations of small molecule cell division inhibitors at low concentrations to affect inhibition of cell division and cell growth. First, the combinatorial approach allows lower doses of each inhibitory molecule, and lower total doses, to be used in animal models and in clinical settings. This alone would decrease side effects of toxic molecules. A combination treatment approach with lower doses of inhibitory molecules makes available even low potency molecules as effective anti-bacterial agents. This broadens the number of anti-bacterial agents available for effective anti-bacterial therapy. Using small molecules at low concentrations is further expected to increase the selectivity of the screening assays by minimizing binding of the small molecules to low affinity, secondary targets in the bacterial cell.

Using a combination of more than one molecule has an added benefit of significantly reducing the risk of spontaneous resistance arising in bacteria. For example, binary, ternary, or quaternary, etc., combination treatments would reduce the likelihood of resistance arising against any one molecule. It is also possible that a combination therapy approach could extend the utility of molecules to which increased rates of spontaneous resistance already exist. Using such molecules in combination could broaden and enhance their utility.

As is known to one of ordinary skill in the art, when the inhibitory or killing effects of two or more antimicrobial used together are significantly greater than would be expected from their effects when used individually, syngerism, or synergy, is said to result. Certain preferred combinations of cell division inhibitors may thus be said to exhibit synergism. Synergism for two compounds may be defined as occurring when there is a reduction in the MIC or MBC or each drug when used in combination versus when used alone. For purposes of the present invention, a combination in which there is a reduction in the MIC or MBC of each drug by at least a factor of two when present in combination versus when present alone is said to exhibit two-fold synergism. Similarly, a combination in which there is a reduction in the MIC or MBC of each drug by at least a factor of four when present in combination versus when present alone is said to exhibit four-fold synergism. In particularly preferred embodiments, the small molecule inhibitors can be used in combination at concentrations significantly lower than their individual minimal inhibitory concentrations (MICs), e.g., lower by a factor of 2, 4, 8, 10, etc. The interaction between two or more compounds may be expressed as the fractional inhibitory concentration (FIC) index, which can be defined as follows (see Katzung, B. (ed.) *Basic and Clinical Pharmacology*):

$$FIC_{index} = FIC_A + FIC_B$$
$$FIC_A = \frac{MIC \text{ of drug } A \text{ in combination}}{MIC \text{ of drug } A \text{ alone}}$$
$$FIC_B = \frac{MIC \text{ of drug } B \text{ in combination}}{MIC \text{ of drug } B \text{ alone}}$$

The fractional bactericidal concentration (FBC) may be similarly defined by substituting MBCs for MICs in the above expressions. Certain preferred compound combinations exhibit an FIC index of less than or equal to 0.5.

It is noted that, as used herein, the term "combination" is not intended to indicate that compounds must be present in, or administered to a subject as, a single composition of matter, e.g., as part of the same dosage unit (e.g., in the same tablet, capsule, pill, solution, etc.) although they may be. Instead, in certain embodiments of the invention the compounds are administered individually but concurrently. As used herein the term "coadministration" or "concurrent administration" of two or more compounds is not intended to indicate that the compounds must be administered at precisely the same time. In general, compounds are coadministered or administered concurrently if they are present within the body at the same time in less than de minimis quantities, i.e., they are each present within the body in detectable quantities that may be sufficient to have a detectable biological effect or response. Accordingly, the compounds may, but need not be, administered together as part of a single composition. In addition, the compounds may, but need not be, administered simultaneously (e.g., within less than 5 minutes, or within less than one minute) or within a short time of one another (e.g., less than an hour, less than 30 minutes, less than 10 minutes, approximately 5 minutes apart). According to various embodiments of the invention compounds administered within such time intervals may be considered to be administered at substantially the same time. One of ordinary skill in the art will be able to readily determine an appropriate time interval between administration of the compounds so that they will each be present at more than de minimis levels within the body or, preferably, at effective concentrations within the body, it being understood that the effective concentration of each compound may be lower when the compounds are used in combinatio than when they are administered individually. For example, two compounds may be administered concurrently if the time interval between doses of the two compounds is less than or equal to 1, 2, 4, 8, 12, 16, 20, 24, or 48 hours.

Standard pharmacokinetic studies can be performed to establish preferred dosing regimens and time intervals. For example, when administering two or more inhibitors of cell division (or one or more inhibitors of cell division and one or more antibiotic agents that act by a mechanism other than inhibition of cell division) it is preferable to administer the compounds sufficiently close together in time to achieve concentrations adequate to result in enhanced activity of compounds relative to their individual activities at the same concentration.

Of course one way of assuring that compounds will be present within the body at appropriate concentrations within the same window of time is to administer the compounds together in a single composition. Thus the invention provides compositions comprising a plurality of cell division inhibitors, e.g., 2, 3, or 4 cell division inhibitors, wherein the individual inhibitors are present within the composition at appropriate proportions so as to achieve a desirable ratio of concentrations within the body, e.g., a concentration of each molecule that is below its MIC but is sufficient to achieve a desired degree of growth inhibition of a target organism when present in the body together with the other active compounds of the composition.

In particular, the invention provides a composition comprising: a plurality of compounds comprising at least a first compound and a second compound, wherein at least one of the compounds inhibits bacterial cell division when provided at a first concentration at or above its MIC (i.e., at least one of the compounds inhibits bacterial cell division when provided alone at a first concentration at or above its MIC), and wherein contacting bacteria with a composition comprising the first compound at a first concentration below its MIC and the second compound at a second concentration below its MIC decreases bacterial growth or survival to a greater extent than contacting the bacteria with the first compound at the first concentration or the second compound at the second concentration. Preferably the plurality of compounds inhibits bacterial survival or proliferation by at least 45%, 50%, 60%, 70%, 80%, 90%, 95%, 99%, or even 100% when the first and second compounds are provided at the first and second concentrations respectively. It is noted that the numerical values are not intended to limit the invention.

In certain of the inventive compositions at least one of the compounds inhibits FtsZ. For example, the compound may inhibit FtsZ GTPase activity, FtsZ in vitro protofilament assembly, or both. In certain inventive compositions at least one of the compounds does not inhibit FtsZ GTPase activity. For example, the compound may inhibit cell division by a mechanism other than inhibition of FtsZ GTPase activity. In certain inventive compositions at least one of the compounds does not inhibit FtsZ in vitro protofilament assembly. In certain inventive compositions at least one of the compounds inhibits FtsZ ring assembly in vivo, either with or without affecting FtsZ GTPase activity and/or protofilament assembly in vitro. In certain embodiments of the invention at least one of the compounds is an FDA-approved antibiotic, e.g., a beta-lactam antibiotic. Certain preferred compositions exhibit the property that the sum of the first concentration and the second concentration is lower than the MIC of either the first or second compounds. Certain of the inventive compositions exhibit the property that the compounds exhibit synergism, e.g., two-fold synergism, four-fold synergism, etc. In certain of the compositions the compounds exhibit an FIC of less than or equal to 0.5. Certain inventive compositions further comprise a third compound, wherein contacting bacteria with a composition comprising the first compound at a first concentration below its MIC and the second compound at a second concentration below its MIC and the third compound at a third concentration below its MIC results decreases bacterial growth or survival to a greater extent than contacting the bacteria with the first candidate compound at the first concentration or the second candidate compound at the second concentration or the third compound at the third concentration.

In certain preferred embodiments of the present invention, one or more of the identified FtsZ GTPase activity inhibitors and one or more identified cell division inhibitory molecules that do not inhibit FtsZ GTPase activity are administered concomitantly with each other. In other preferred embodiments, the FtsZ GTPase activity inhibitor and/or other cell division inhibitor that does not inhibit FtsZ GTPase activity identified in the in vitro and/or in vivo assays of the invention can be administered concomitantly with already identified and clinically proven antimicrobial agents, such as antibiotics approved by the U.S. Food and Drug Administration (FDA) or a similar regulatory agency. A wide variety of such agents are known as described, for example, in *Goodman and Gilman's The Pharmacological Basis of Therapeutics*, 10$^{th}$ Ed. McGraw Hill, 2001, and Katzung, B. (ed.) *Basic and Clinical Pharmacology*, McGraw-Hill/Appleton & Lange; 8th edition (Sep. 21, 2000), both of which are incorporated herein by reference. For example, one of the conserved bacterial cell division genes is ftsI, which codes for penicillin-binding protein 3 (PBP3). FtsZ-specific and FtsZ non-specific septation inhibitors identified in this assay can be combined with beta-lactam antibiotics that have high affinity for the septation-specific molecule PBP3.

The invention provides a method for identifying a preferred combination of compounds that affects cell growth or division, comprising steps of: (a) contacting bacteria with a plurality of candidate compounds comprising at least a first compound and a second compound, wherein the first compound is provided at a first concentration that is below its minimum inhibitory concentration (MIC) and the second compound is provided at a second concentration that is below its MIC, and wherein at least one of the candidate compounds inhibits bacterial cell division when provided in the absence of other candidate compounds at a concentration at or above its MIC; (b) measuring bacterial survival or growth; and (c) identifying the compound combination as a preferred compound combination if bacterial survival or growth is decreased to a greater extent by the plurality of candidate compounds than by the first candidate compound when provided at the first concentration or by the second candidate compound when provided at the second concentration.

It will be appreciated that any of a number of different assays may be used to measure bacterial survival or growth including, for example, assessing the turbidity of a culture (either visually or by measuring optical density), measuring incorporation or uptake of a labeled compound such as a radiolabeled precursor molecule (e.g., nucleotide, amino acid, etc.). A variety of cell types may be used, including various bacterial strains bearing mutations in ftsZ, other genes involved in cell division or other cellular processes, etc. Cells expressing a detectable marker can be employed, which may facilitate quantitation. Preferred combinations identified using the inventive method may inhibit (e.g., prevent or reduce) bacterial survival or proliferation by 45%, 50%, 60%, 70%, 80%, 90%, 95%, 99%, or even 100%, relative to bacterial survival or proliferation in the absence of the compounds at the selected concentrations. For example, cell number may be reduced by 45%, 50%, 60%, 70%, 80%, 90%, 95%, 99%, or even 100% in the presence of the compound versus in its absence. One non-limiting method to measure cell growth is to dilute cells to a low density and then add a candidate compound or compounds to the culture vessel. The cells are incubated under appropriate conditions for growth, and the increase (or lack thereof) in cell number over time is assessed. Other methods known to one of ordinary skill in the art can also be used. It is noted that the listing of numbers is merely exemplary and not intended to limit the invention.

The invention further provides a method of inhibiting cell growth or survival comprising the step of administering to the cell a plurality of compounds comprising at least a first compound and a second compound, wherein at least one of the compounds inhibits bacterial cell division when provided at a concentration at or above its MIC, and wherein contacting bacteria with the first compound at a first concentration below its MIC and the second compound at a second concentration below its MIC decreases bacterial growth or survival to a greater extent than contacting the bacteria with the first compound at the first concentration or the second compound at the second concentration. The cells may be, for example, bacterial cells, fungal cells, protozoal cells, etc.

In certain embodiments of the method, the contacting step is performed by administering the plurality of compounds to a subject, e.g., a mammalian subject such as a human being, suffering from infection, such that the compounds are present at first and second concentrations within the body. Any of the inventive compound combinations identified according to the methods described herein may be used, including compositions comprising a plurality of compounds such as those described above. The compounds may be administered individually, e.g., concurrently, or together as a single composition. It may be desirable to monitor serum concentrations of the compounds to ensure that they are present at desirable concentrations within the body. Depending on the site of infection, it may be desirable to achieve specific concentrations in different compartments of the body. For example, it may be desirable to achieve specific concentrations in the blood, urine, cerebrospinal fluid, etc. It may be desirable to achieve specific concentrations in target organs such as the liver, lung, heart, kidney, skin, etc., or within sites of infection or potential infection such as wounds, abscesses, etc. In order to achieve such target concentrations in organs it may be necessary to employ significantly higher concentrations in the bloodstream. One of ordinary skill in the art will be able to adjust the dosages appropriately.

In certain embodiments of the methods and compositions described above, at least one of the compounds inhibits FtsZ GTPase activity and/or protofilament assembly. In certain embodiments of the methods and compositions at least one of the compounds does not inhibit FtsZ GTPase activity and/or does not inhibit FtsZ protofilament assembly. In certain embodiments of the invention at least one of the compounds that does not inhibit FtsZ GTPase activity and/or does not inhibit FtsZ protofilament assembly inhibits cell division by a mechanism other than inhibition of FtsZ GTPase activity and/or protofilament assembly. In certain embodiments of the invention at least one of the compounds stabilizes FtsZ protofilament assembly. Whether a particular compound inhibits FtsZ GTPase activity can be assessed either in vitro or in vivo, or both. Compounds that exhibit inhibition of FtsZ GTPase activity in vitro and/or in vivo can be used. Similarly, whether a particular compound inhibits or stabilizes FtsZ protofilament assembly can be assessed using in vitro or in vivo assays, or both. Compounds that exhibit inhibition or stabilization of FtsZ GTPase protofilament assembly in vitro and/or in vivo can be used.

Certain preferred compound combinations inhibit cell survival and/or proliferation at concentrations wherein the sum of the first concentration and the second concentration is lower than the MIC of either the first or second compounds. In certain preferred combinations the concentration of at least one of the compounds is at least 4-fold lower than its MIC, at least 10-fold lower than its MIC, etc.

Pharmaceutical Compositions

As described above, the present invention provides compounds useful for the treatment of microbial infections and/or disorders relating to a microbial infection. It will be appreciated that the compounds of the present invention can exist in free form for treatment, or where appropriate, as a pharmaceutically acceptable derivative thereof. Additionally, it will be appreciated that one or more of the inventive compounds can be formulated with a pharmaceutically acceptable carrier or excipient to provide a pharmaceutical composition.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-microbial compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.1% and not more than 50% by weight based on the total weight of the composition, including carrier medium and/or auxiliary agent(s). Preferably, the proportion of active agent varies between 0.1 to 5% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers for medicaments may all be suitable as carrier media.

The compounds of the invention may be administered using any amount and any route of administration effective for attenuating infectivity of the microorganism. Thus, the expression "amount effective to attenuate infectivity of a microorganism", as used herein, refers to a nontoxic but sufficient amount of the anti-microbial agent to provide the desired treatment of microbial infection. The exact amount required will vary from subject to subject, depending on the species, age, and general condition of the subject, the severity of the infection, the particular anti-microbial agent, its mode of administration, and the like. The anti-microbial compounds of the invention are preferably formulated in dosage unit form for ease of administration and uniformity of dosage. The expression "dosage unit form" as used herein refers to a physically discrete unit of anti-microbial agent appropriate for the patient to be treated.

Each dosage should contain the quantity of active material calculated to produce the desired therapeutic effect either as such, or in association with the selected pharmaceutical carrier medium. Typically, the anti-microbial compounds of the invention will be administered in dosage units containing from about 5 mg to about 500 mg of the anti-microbial agent with a range of about 0.1 mg to about 50 mg being preferred.

The compounds of the invention may be administered orally, parenterally, such as by intramuscular injection, intraperitoneal injection, aerosol, intravenous infusion or the like, depending on the severity of the infection being treated. The compounds of the invention may be administered orally or parenterally at dosage levels of about 0.1 mg/kg to about 50 mg/kg and preferably from about 2 mg/kg to about 25 mg/kg, of patient body weight per day, one or more times a day, to obtain the desired therapeutic effect.

According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

As described above, the pharmaceutical compositions of the present invention additionally comprise a pharmaceutically acceptable carrier, which, as used herein, means a non-toxic, inert solid, semi-solid or liquid filler, diluent, encapsulating material or formulation auxiliary of any type. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutical Compositions

According to the methods of treatment of the present invention, microbial infections are treated or prevented in a patient or organism such as a human, lower mammal, fish, bird, or other organism, by administering to the patient a therapeutically effective amount of a compound or pharmaceutical composition of the invention, in such amounts and for such time as is necessary to achieve the desired result. In certain preferred embodiments, the compounds of the present invention are capable of acting as broad spectrum antibiotics and are effective against Gram-negative bacteria. By a "therapeutically effective amount" of a compound of the invention is meant a sufficient amount of the compound to treat microbial, e.g., bacterial infections, at a reasonable benefit/risk ratio applicable to any medical treatment. It will be understood, however, that the total daily usage of the compounds and compositions of the present invention will be decided by the attending physician within the scope of sound medical judgment.

As discussed above and as exemplified in greater detail below, the compounds of the present invention are useful as anti-microbial agents, and thus may be useful in the treatment or prevention of microbial infections. As used herein, unless otherwise indicated, the terms or phrases "microbial infection" and "disorder relate to a microbial infection" include, but are not limited to, infection by the following, bacterial, fungi, yeast, or protozoa.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another antibiotic), or they may achieve different effects (for example, surgery for removal of a tumor, administered concurrently with an inventive antibiotic).

In but one example of the usefulness of combination therapy, it has been shown that treatment with an antibiotic appears to have protective effects against atherosclerosis complications. Specifically, it has been shown that infection with *Chlamydia pneumoniae* is a contributing factor in the pathogenesis of atherosclerosis (Movahed, M. R. *J.S.C. Med. Assoc.* 1999, 95, 303). *C. pneumoniae* and its constituents, such as specific antigens and even DNA, have been detected in atherosclerotic plaques and also in endothelium, smooth muscle cells, and macrophages of arterial walls with atherosclerosis, but have not been found in normal arteries. Thus, treatment with an antibiotic may be used in combination with other therapies, such as surgery or other medication, to more effectively mitigate the symptoms of this disorder.

In yet another aspect, the present invention also provides a pharmaceutical pack or kit comprising one or more containers filled with one or more of the ingredients of the pharmaceutical compositions of the invention, e.g., one or more compounds, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

The invention provides a unit dosage form containing one or more compounds that inhibit bacterial growth. The compounds may be one or more of the compounds described herein and/or one or more compounds identified according to the inventive screening method. The compounds may inhibit FtsZ. "Unit dosage form" refers to physically discrete units suited as unitary dosages for the subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dosage form may be, for example, a volume of liquid (e.g,. a pharmaceutically acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dosage form may contain a variety of components in addition to the therapeutic agent(s). For example, pharmaceutically acceptable carriers, diluents, stabilizers, buffers, preservatives, etc., may be included. In certain embodiments of the invention the unit dosage form contains at least two compounds, each of which inhibits bacterial growth and at least one of which inhibits FtsZ, wherein the absolute and/or relative amounts of the compounds are selected so that the combination produces a desired effect while using lower amounts of each agent than the amount of either agent that would be required to produce an equivalent effect if the agent was administered as sole antibiotic therapy for the disease, disorder or condition or was administered in combination with a therapeutic agent for treating the disease, disorder, or condition that does not significantly inhibit FtsZ at the dose employed (e.g., less than 1% inhibition, or less than 5% inhibition). In certain embodiments of the invention the unit dosage form contains at least two compounds, each of which inhibits FtsZ, such that the combination produces a desired effect while using a lower total amount of therapeutic agent than the amount of either agent that would be required to produce an equivalent effect if the agent was administered as sole antibiotic therapy for the disease, disorder, or condition or was administered in combination with a therapeutic agent for treating the disease, disorder, or condition does not significantly inhibit FtsZ at the dose employed. The amounts may be selected to produce fewer or less severe side effects than would occur if either agent was used as sole therapy or was used in combination with a therapeutic agent that does not significantly inhibit FtsZ at the dose employed.

Information Obtained from Screens

The invention further provides a computer-readable medium containing, e.g., storing, information obtained from performing any of the screening methods of the invention, regardless of where such screening methods were practiced. The medium may be, e.g., a hard disc, compact disc, floppy disc, read-only memory, read/write memory, flash memory, magnetic tape, etc. The invention further provides a system comprising the computer-readable medium and a computer capable of processing, displaying, or manipulating the information. The information can be expressed in any convenient format. Typically the information will be stored in a database. The information may, for example, identify compounds and/or compound combinations by name, structure, identication number, or any other suitable means. The information may identify bacteria whose growth is inhibited by the compounds or compound combinations and may include concentrations, growth rates, etc. The bacteria may be identified in any suitable manner, e.g., by name, by accession number, or descriptively. The information may identify one or more compounds or compound combinations that inhibit growth of a particular bacterium. The information may describe the extent to which FtsZ activity and/or bacterial growth is inhibited by one or more concentrations of the compound(s), either in vitro or in vivo. The information may describe the effect of administering one or more compounds to an animal to whom an infectious agent has been administered or that is suffering from an infectious disease. The information can be qualitative or quantitative.

The invention further provides a computer or other electronic device capable of processing, transmitting, or receiving the information and also includes a method comprising the step of transmitting, receiving, and/or processing the information, preferably by electronic means or using the information in a concrete and substantial manner, regardless of where the information was originally gathered. The invention further provides a method comprising the step of testing a compound identified according to any of the methods described herein either in a cell-based assay, in an animal model (e.g., an animal model of disease), or in a human subject, or of synthesizing or modifying a compound identified according to any of the methods described herein.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance that can be adapted to the practice of this invention in its various embodiments and the equivalents thereof.

EXAMPLES

Example 1

In Vivo Assay for FtsZ Inhibitors or Activators

Materials and Methods

Differential in vivo screens were carried out at 30° C. by looking for greater than or equal to 45% growth inhibition and phenotypic aberrations (e.g., changes in filamentation or cell shape (e.g., rod to sphere) or minicell formation) in the *E. coli* DRC39 strain, which is deleted for the multidrug efflux pump AcrAB, and its congenic ftsZ84 variant DRC40. Libraries were screened with two different concentrations of compound using 40- and 200 nl pin transfer devices.

Figure 21:
FIG. 21 shows a Cartesian pin transfer robot, a pin array, and a fluorescence plate reader that may be used to perform high-throughput screening with various assays of the invention.

Bacterial cultures were grown overnight at 30° C. in 0.5% NaCl Luria Broth (LB) with 20 μg/ml kanamycin and diluted 1:1000 ($OD_{600}$ of 0.005) in fresh 0.5% NaCl LB. The Labsystems 384-well liquid dispenser was used to dispense 40 μl of the diluted culture to the first 23 columns of a clear NUNC 384-well plate, leaving one column empty for manual addition of the blank samples. 200 nl or 40 nl of compounds were transferred from a 384-well library plate to the assay plate using a Cartesian pin-transfer robot (see FIG. 21). After compound addition, 40 μl of LB-Amp (50 μg/ml) was added in quadruplicate to the empty column of each plate, serving as blanks. For the DMSO-only control, 1 μl of 10% DMSO was added in quadruplicate to wells lacking compounds.

5 μM 26-E10, a compound that had been shown to cause filamentation in *E. coli* cells, was added as a positive control for inhibition of bacterial cell division. This compound was initially identified in an in vitro screen for inhibitors of FtsZ GTPase activity. Subsequent experiments revealed that these results were artifactual and that 26E-10 lacks detectable effects on FtsZ GTPase activity at the concentrations tested. However, following its artifactual identification in the in vitro screen, it was observed that 26E-10 inhibited cell growth and caused cell filamentation. In addition to its use as a positive control in the in vivo screens, 26E-10 was also identified as a hit in these screens, since it was, of course, present in the library.

After the controls were set up, the plates were incubated at 30° C. in a humidified chamber. At 24 hours and 48 hours, the Wallac Victor Multiwell Plate Reader measured the absorbance (650 nm) of each well. The data for each plate was processed in Microsoft Excel in order to yield a list of each well ranked in order of increasing turbidity. We then inspected microscopically samples from wells that showed 45-50% or greater growth inhibition looking for filamentation or minicells, phenotypes one would expect upon perturbation of the cell division process. Cells were visualized with DIC microscopy at 100× magnification using the Zeiss Axiophot Microscope.

Results

In an initial screen, a total of 18,320 compounds from two different libraries (Chembridge 16,320-member small molecule library and the ~2000 member NCI mini diversity library) were screened against the wild-type and temperature-sensitive *E. coli* strains. A compound that caused greater than or equal to 45% decrease in turbidity of the culture in a well was considered a "hit." There were 98 compounds that caused 45% or greater growth inhibition in the wild-type strain and 173 hits against the temperature-sensitive strain. Exactly 81 of the hits caused virtually complete growth inhibition/lysis in both strains, indicating that they are highly potent and may affect other targets required for cell viability in addition to, or besides the cell division process (see FIG. 10).

We also observed that 92 compounds only exhibited a marked effect in the temperature sensitive strain, of which 27 compounds caused cells to form long filaments. These molecules are of particular interest as they support the original hypothesis that the mutant will be more sensitive to the effects of compounds that target the cell division machinery, than the wild-type strain. Interestingly, there were 17 compounds that affected the wild-type strain yet did not show any significant effect on the mutant strain. Out of these 17 hits, there were 2 compounds that caused cell filamentation. These compounds could be potential stabilizers of the FtsZ-ring, acting as chemical suppressors of the more labile structure in the temperature-sensitive strain, while effectively hyperstabilizing the FtsZ-ring in the wild-type strain, causing filamentation. This is an exciting possibility. Further in vivo and/or in vitro validation of the hits generated from the in vivo screen may be carried out as described, e.g., in Examples 2 and 3.

In a second round of screening of the two libraries using 100 nl of compound, a total of 190 hits were identified. The compounds were rescreened using 5 nl of compound, identifying a total of 39 hits. Of the 39 hits, 18 inhibited growth greater than or equal to 45% in both the DRC39 and DRC40 strains; 16 inhibited growth greater than or equal to 45% in DRC40 (ftsZ84), but not in DRC39 ($FtsZ^+$); and 5 inhibited growth greater than or equal to 45% in DRC39, but not in DRC40.

The 16 compounds that inhibited growth in only DRC40 may preferentially destabilize Z-rings in ftsZ84 cells, while the 5 compounds that inhibited growth in only DRC39 may have low affinity for the FtsZ84 mutant protein vis-à-vis FtsZ. Alternatively, some of the compounds that inhibited growth in only DRC39 may bind and stabilize the mutant Z-ring in DRC39 cells, whereas such stabilization may hinder the constriction of the wild-type Z-rings in DRC39 cells, thus blocking cell growth and division. This scenario would be similar to the differential effects of stabilization of Z-rings in wild-type (constriction blocked) and in ftsZ84 mutant cells (suppression of thermosensitivity) by higher dosage of the essential division protein ZipA. Table 1 presents the number of compounds showing each of the major division-related phenotypes associated with the in vivo hits.

TABLE 1

Major division-related phenotypes associated with the in vivo hits.

| Phenotypic Data | WT (100 nl) | TS (100 nl) | WT (5 nl) | TS (5 nl) |
| --- | --- | --- | --- | --- |
| f | 9 | 16 | 3 | 10 |
| mf | 8 | 11 | 8 | 2 |
| F | 1 | 25 | 1 | 5 |
| mc | 40 | 3 | 1 | 0 | f = mixed population of rods with short filaments;
mf = medium filaments (4X-16X);
F = Long filaments (>16X); and
mc = minicells.
WT = DRC39,
TS = DRC40.

From the combined screens, 54 compounds were selected for follow-up experiments. These compounds fell into 2 categories: 23 molecules reproducibly caused filamentation or minicell formation (in one or both strains), while the rest (31) caused greater than 45% growth inhibition of both strains regardless of the phenotype. A few of the second category molecules induced morphological transitions such as round or sausage-shaped cells.

We have tested all 54 compounds for their effects on FtsZ GTPase activity using the malachite green-phosphomolybdate assay. Surprisingly, only 6 compounds showed significant inhibition of FtsZ GTPase, with $IC_{50}$ values ranging between 10-88 μM. Another 6 in vivo hits induced lethal cell filamentation with no effect on FtsZ GTPase activity, suggesting that they may target other essential components of the division machinery in bacteria.

Example 2

Figure 22:
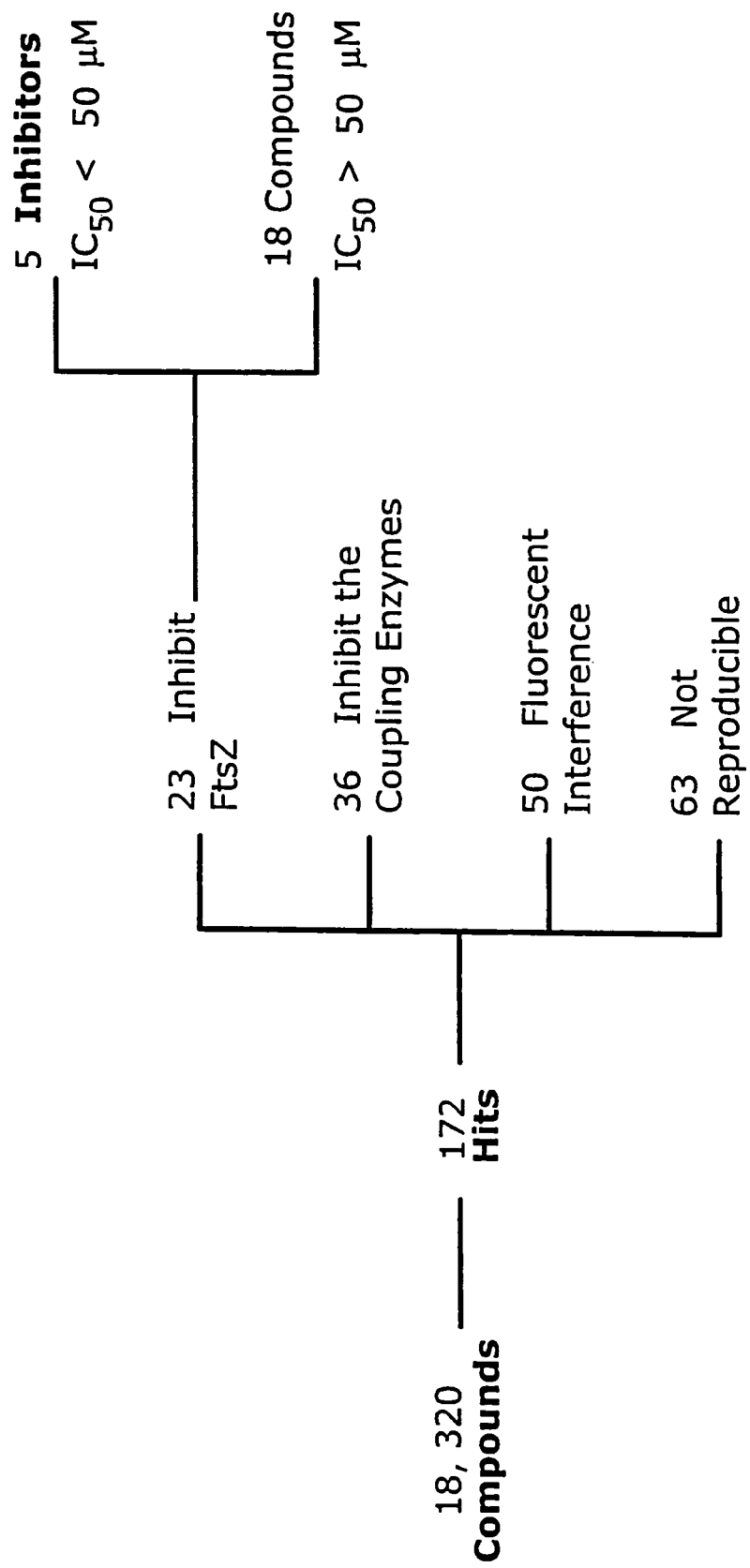
FIG. 22 is a flow chart that depicts results obtained in the in vitro FtsZ screen that was carried out to identify inhibitors of FtsZ GTPase activity.

In Vitro Assays and Effect of an Inhibitor Identified In Vitro on FtsZ In Vivo This example describes various in vitro assays that were used to identify FtsZ GTPase inhibitors in a primary screen (NADH assay) and to verify preferred inhibitors in secondary assays (charcoal-based assay, TLC assay). FIG. 22 is a chart showing the overall in vitro screening process that was used to identify 5 inhibitors of FtsZ GTPase activity and results obtained. The example further describes the in vivo effects of one inhibitor identified in vitro.

NADH Assay

Figure 24:
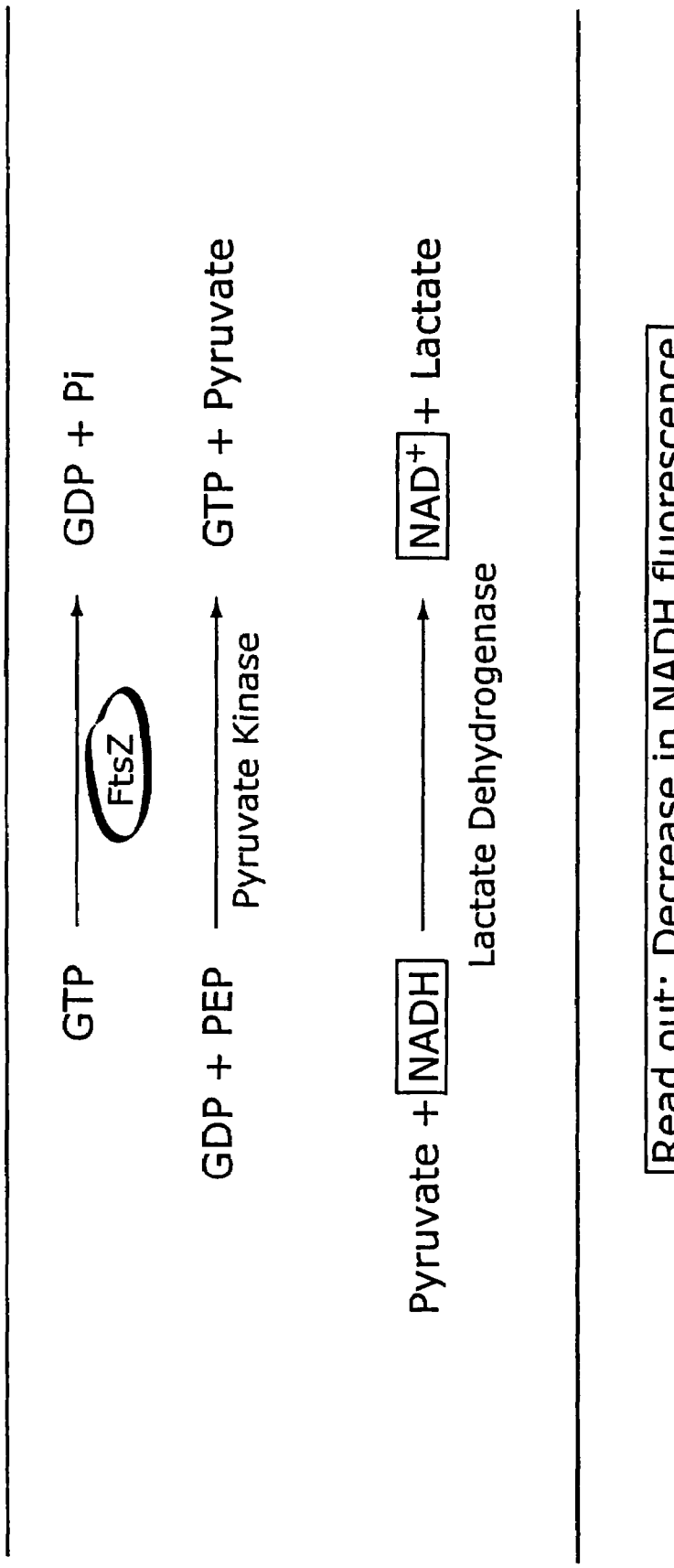
FIG. 24 illustrates the in vitro enzyme-coupled assay for assembly dependent FtsZ GTPase activity.

An enzyme-coupled assay for assembly-dependent FtsZ GTPase activity was developed and utilized to screen two compound libraries, as described below and shown in FIG. 24. According to the assay, purified FtsZ protein is combined in a reaction vessel with the enzymes pyruvate kinase and lactate dehydrogenase, and the substrates GTP, PEP, and NADH. Upon reaction with GTP, FtsZ yields the products GDP and phosphate, providing a substrate, GDP, for pyruvate kinase in combination with PEP to generate pyruvate. Pyruvate in turn becomes a substrate for lactate dehydrogenase with NADH to yield $NAD^+$ and lactate. Test molecules are added to the reaction mixture to assess their effect on FtsZ activity. Activation of FtsZ activity can be determined by measuring a decrease in the rate of NADH fluorescence compared to the absence of the test molecule (excitation: 355 nm, emission: 460). This assay was miniaturized by testing compounds in a multi-well plate and assessing fluorescence using a Wallac plate reader.

The assay was miniaturized for high throughput screening of the Chembridge 16,320-member small molecule library and the ~2000 member NCI mini diversity library against untagged, assembly-competent FtsZ purified from *Escherichia coli*, using multi-well plates and assessing fluorescence with a Wallac plate reader. The reaction mixture contained 1 mM PEP, 200 μM NADH, 68 IU/ml pyruvate kinase, 68 IU/ml L-lactate dehydrogenase, 0.1% Tween 20, and 2 μM FtsZ (*E. coli*) in assembly buffer E (50 mM MOPS, pH 6.5, 50 mM KCl, 5 mM $MgCl_2$). 25 μl reaction mixture was dispensed per well of 384-well plates (Labsystems Cliniplate), with one column designated for controls. 100 nl library compounds (in dimethyl sulfoxide, DMSO) were robotically pin-transferred from 384-well library plates to the assay plates such that the final concentrations ranged between 20-50 μM, depending on the molecular weights of compounds. Control wells received either 0.3% DMSO, or $AlF_4^-$ which was previously shown to inhibit FtsZ GTPase. The reactions were initiated at ~28° C. by adding 1 mM GTP to the wells and monitored over 25-40 min by the decrease in fluorescence emission as NADH underwent oxidation (355 nm excitation, 460 nm emission).

From this screen, 172 compounds were identified, of which 5 compounds that reproducibly and robustly inhibited FtsZ GTPase activity were verified using additional screens. These 5 inhibitors (58-P18 (NCI Diversity library), 16-L09 (Chembridge library), 18-M04, 27-D12 (Chembridge library), and 27-F02 (Chembridge library)) of FtsZ GTPase activity are depicted in FIG. 11. As noted in Example 1, 26E-10 was artifactually identified in the initial screen but later proved not to be an inhibitor of FtsZ GTPase activity at the concentrations tested.

Charcoal Based Assay for FtsZ GTPase Activity

A charcoal-based radioactive assay to measure FtsZ GTPase activity was adapted from Lee, et al. (1992), referenced above. After a 5 min preincubation of *E. coli* FtsZ protein with the inhibitors at 30° C., the reactions were initiated by adding 1 mM [γ-$^{32}$P] GTP (200-500 cpm/pmol). At specific time points, 6-μl aliquots were withdrawn and added to 600 μl of 5% (w/v) activated charcoal in 50 mM $NaH_2PO_4$. Samples were immediately vortexed and placed on ice. All samples were centrifuged at 14,000 rpm for 20 min to pellet the charcoal and 80 μl supernatants were withdrawn for quantification of $^{32}P_i$ by scintillation counting. The turnover rate of FtsZ GTPase was calculated using values from the linear phase of GTP hydrolysis and percent inhibition was determined by comparing rates of hydrolysis in the presence or absence of inhibitors.

TLC Assay

Another such assay used to validate the primary hits is the radioactive thin-layer chromatographic (TLC) analysis, which measures the conversion of [α-$^{32}$P]GTP to [α-$^{32}$P]GDP catalyzed by FtsZ. In this assay, the two nucleotides (GTP and GDP) are present in reaction aliquots and are separated on a polyethyleneimine-cellulose thin-layer plate. This affords rapid and direct estimation of the GTPase activity of FtsZ under reaction conditions that are known to promote FtsZ assembly. The reaction mixture does not contain other enzymes or substrates unlike the situation with the enzyme-coupled assay used for primary screening. Therefore, the TLC assay result is a reliable indicator of the in vitro efficacy of the candidate molecules identified as hits using the coupled assay.

TLC analysis of FtsZ GTPase activity in the presence or absence of test compounds was also conducted. 5 μM FtsZ was incubated with 1 mM [α-$^{32}$P]GTP (1.5 μCi) at 30° C. and 2 μl aliquots were withdrawn at 5, 15, and 30 min intervals into an equal volume of 1% SDS-20 mM EDTA to quench the reaction. The aliquots were incubated at 70° C. for 2 minutes prior to spotting 0.5 μl samples on a PEI-cellulose plate. The TLC plate was developed in 0.75 M potassium phosphate buffer (pH 3.4), air-dried, and exposed to a film or a phosphorimager.

Malachite Green-Phosphomolybdate Assay $IC_{50}$ values for the effect of various compounds on *E. coli* FtsZ (FtsZEc) and on *M. tuberculosis* FtzZ (FtsZ$_{Mt}$) GTPase activity obtained using the malachite green-phosphomolybdate assay (Akiyama, Y., Kihara, A., Tokuda, H. and Ito, K. 1996, J. Biol. Chem. 271:31196-31201, incorporated herein by reference) are shown in Table 2. FtsZ was preincubated with varying concentrations of compounds or with 3% DMSO in buffer E for 5 min at 30° C., before adding 1 mM GTP to the reactions. Reaction kinetics were followed by measuring inorganic phosphate released upon GTP hydrolysis. The IC50 values were extrapolated from log dose-response curves and are averages from three independent determinations.

TABLE 2

$IC_{50}$ values of in vitro inhibitors against FtsZ$_{Ec}$ and FtsZ$_{Mt}$ GTPases

| Compound | $IC_{50}$ (μM) | |
|---|---|---|
| | FtsZ$_{Ec}$ | FtsZ$_{Mt}$ |
| 27D12 | 5 | 55 |
| 27F02 | 10 | 70 |
| 16L09 | 15 | 50 |

TABLE 2-continued

IC$_{50}$ values of in vitro inhibitors against FtsZ$_{Ec}$ and FtsZ$_{Mt}$ GTPases

| | IC$_{50}$ (μM) | |
|---|---|---|
| Compound | FtsZ$_{Ec}$ | FtsZ$_{Mt}$ |
| 18M04 | 25 | >100 |
| 58P18 | 4 | 30 |

In Vivo Effects of an Inhibitor Identified In Vitro

The effect of the inhibitor 58P-18, which was identified and verified using the in vitro assays described in this example, on Z-ring assembly and cell division was tested in DRC39 cells in a similar manner as that described above for 26E-10. FIG. 12 shows that cells start elongating within 60 min of treatment with 40 μM 58P-18 and, more strikingly, none of the treated cells appear to contain a medial FtsZ ring. Even though DAPI staining shows that the nucleoids have replicated and segregated in the presence of the compound, none of the short cells in the field has been able to assemble a Z-ring between segregated nucleoids. Instead, the GFP fluorescence is delocalized all over the cell body (fluorescence is much more intense than in the control cells, similar to that seen with 26E-10), suggesting the possibility of aberrant FtsZ-GFP polymerization. Interestingly, in contrast to 26E-10, treatment with 58P-18 seems to generate a pattern of FtsZ-GFP distribution in cells that is very similar to that seen with DAPI stained nucleoids. Thus, without limiting the mechanism of the invention, 58P-18 may promote inappropriate association of FtsZ with the chromosome. It is noted that the enhanced background due to 58P-18 auto-fluorescence, interpretation of these data may be subject to revision or qualification.

Example 3

In Vitro and In Vivo Analysis of Compound 26E-10

Below are shown the MIC values of 26E-10, which causes filamentation in both DRC39 and DRC40 but has no evident effect on FtsZ GTPase activity in vitro, for various bacterial species.

TABLE 3

MIC values for 26E-10 against different bacterial species and strains.

| Organism | MIC (μM) |
|---|---|
| E. coli MC1000 (wild-type) | >40 |
| E. coli DRC39 (ΔacrAB::kan) | 10 (filaments) |
| E. coli DRC40 (DRC39 ftsZ84) | 2.5* (filaments) |
| E. coli DRC42 (DRC39 recA::cat) | 10 |
| Vibrio cholerae | 40 |
| Bacillus subtilis | 40 |
| Staphylococcus aureus | 20 |
| Clostridium perfringens | >80 (filaments) |

*This concentration results in a culture with slight turbidity. However, this is believed to represent unlysed filaments rather than bacterial growth.

As also occurred in the case of the in vitro FtsZ inhibitors, 26E-10 permeates E. coli cells significantly better in the absence of the AcrAB pump. Consistent with the in vivo assay, the ftsZ84 mutant is significantly more sensitive to 26E-10 compared to the congenic parent strain.

To rule out the possibility that SOS-mediated SulA induction might be responsible for cell division inhibition by 26E-10, we introduced the null recA::cat allele into DRC39 by P1 transduction. To confirm the absence of the recA gene product in the transductants, we screened them for UV-sensitivity and chose one chloramphenicol-resistant, UV-sensitive transductant, designated DRC42, for testing. RecA is essential for the induction of SOS regulons in E. coli and in its absence, the division inhibitor SulA is not induced. DRC42 was as sensitive to 26E-10 as its parent DRC39 (Table 3), indicating that 26E-10 is unlikely to cause division inhibition via SulA induction.

26E-10 is also active against other wild-type organisms (Table 3). Interestingly, C. perfringens showed a filamentation phenotype in the presence of 80 μM 26E-10 without any overt effect on cell growth under anaerobic conditions. Any of the in vivo or in vitro hits may be tested on DRC42 to rule out indirect inhibition of cell division through SOS induction as well as testing the compounds against a plethora of organisms in broth cultures to check the broad-spectrum nature of the hits.

Effect of Compound on FtsZ Ring Assembly

The effect of an identified small molecule inhibitor, 26E-10, on FtsZ ring assembly was tested in vivo by employing a single-copy ftsZ-GFP fusion construct that was integrated at the phage lambda attachment site on the E. coli chromosome. The wild-type, untagged ftsZ gene was also present on the chromosome at its normal locus. The expression of the fusion gene was placed under the control of a mutationally weakened, IPTG inducible tac promoter. Since the level of FtsZ protein expression in the cell is critical for proper cell division, the fusion gene was expressed from a single-copy and at the lowest possible inducer concentration to generate a low level of fluorescently tagged FtsZ-GFP, which did not cause any noticeable cell division aberrations. However, this low level expression was sufficient for imaging the in vivo assembly of the FtsZ-GFP fusion protein by fluorescence microscopy.

We found that the compound-induced phenotype is more pronounced in an acrAB deletion background, suggesting the likely involvement of the drug pump in reducing the intracellular concentration of compounds such as 26E-10. Therefore, in order to test the effect of 26E-10, a culture of the E. coli K-12 strain MC1000 containing an acrAB deletion (strain DRC39) was grown to early log-phase (~1-2×10$^8$/ml), and 26E-10 was added at its MIC (minimum inhibitory concentration) of 10 μM. Aliquots were withdrawn at 15, 30, 60, and 90 min intervals after the addition of the compound, and the cells in the aliquots were fixed immediately with a mixture of glutaraldehyde and para-formaldehyde. This fixation step was carried out to ensure that the handling of cells before microscopy did not cause any artifactual destabilization of the FtsZ ring structure. The fixed cells were washed with PBS, stained with DAPI to visualize the nucleoids, and observed under a fluorescence microscope. In some experiments, the cells were embedded on a thin layer of agarose before microscopy for ease of visualization. After examining the cells for GFP (FITC filter set) and DAPI (DAPI filter set) fluorescence, the DIC digital images of cell morphology were recorded using Nomarski optics (differential interference contrast, DIC, microscopy). Images were taken using an Olympus fluorescence microscope equipped with a CCD camera. Images were finally imported into Adobe Photoshop for processing and presentation.

As shown in FIG. 17, the control culture (no 26E-10 added) displayed a distinct equatorial FtsZ-GFP ring structure (Z-ring) at the center of the cells. DAPI staining revealed that the cells carrying Z-rings had segregated nucleoids present on either side of the ring. However, upon treatment with 26E-10, DRC39 cells started filamenting (~4× long cells seen within 60 min of treatment), which is indicative of a defect in cell division. Concurrently, the Z-rings appeared markedly reduced in number and diminished in intensity in these elongated cells, with appreciable GFP fluorescence distributed along the length of the cell body. This suggests that 26E-10 is inhibiting de novo Z-ring assembly and/or destabilizing formed ring structures.

It is important to note that the fluorescence intensity in the treated cells was significantly higher compared to the control culture, and the exposure time for imaging the treated cells was 5-10 fold lower than that for the control cells. It is known that aberrant polymerization of FtsZ-GFP fusion in the cell cytoplasm causes the emitted GFP fluorescence to be intense. Even though we could not discern any such aberration under the microscope, it is possible that 26E-10 may induce inappropriate polymers to form.

We would also point out that DAPI staining showed that the filamenting cells contained mostly regularly spaced nucleoids, suggesting that 26E-10 does not affect DNA replication or chromosome segregation. However, DAPI staining of the elongated cells was not uniform because the cells were fixed but not permeabilized. To avoid this problem, blue Hoechst 33342 dye, which efficiently stains nucleoids in unpermeabilized $E.$ $coli$ cells, was used.

FIG. 18 shows two fields of a 26E-10 treated culture. Images were captured as described above. After 90 min treatment: there was a mixture of 1× to 8× long cells and most of the cells were devoid of distinct Z-rings irrespective of their age as evident from the cell length distribution. This indicates that 26E-10 is targeting Z-ring assembly and the effect increases in severity with the time of treatment. The fact that there were 1× cells in the culture indicates that cell division was continuing at a low level presumably because Z-rings were stochastically forming in some cells in the presence of 26E-10 and some of these rings could complete the septation process.

Genetic Evidence of Inhibition of Cell Division In Vivo

Figure 20:
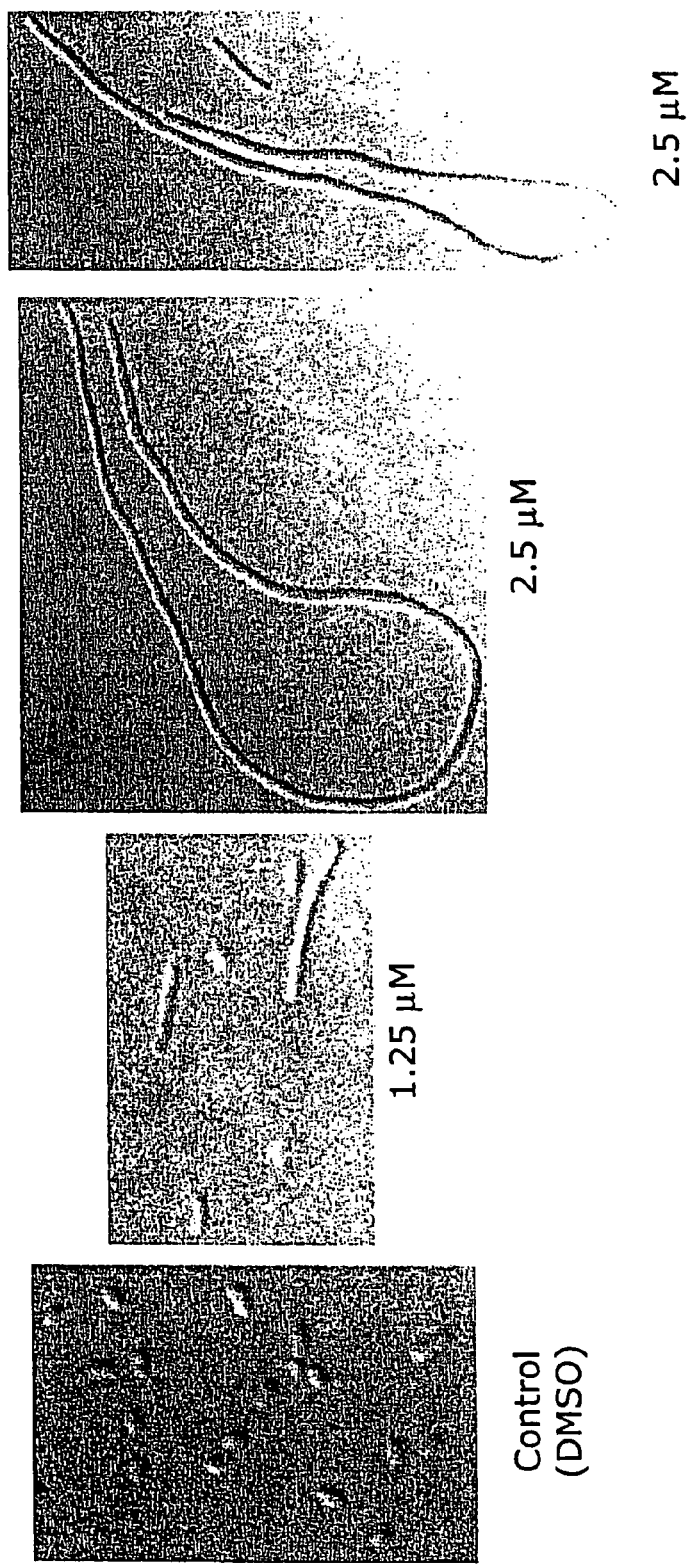
FIG. 20 shows images that illustrate that compound 26E-10 causes chemical synthetic lethality in ftsZ84-ts *E. coli* cells (acrAB-null)/pBR322 at 30° C.

Results presented in FIG. 20 provide an additional cell biology perspective on the effect of 26E-10 in $E.$ $coli$ cells. In order to understand whether 26E-10 indeed targets septation in vivo, it was tested on the thermosensitive ftsZ84 mutant of $E.$ $coli$. This mutant is conditional-lethal because it grows and divides at 30° C. but undergoes a cell division block at 42° C. that leads to lethal cell filamentation. The division block of the ftsZ84 mutant at 42° C. is due to a drastic destabilization of the Z-rings at high temperature (within a minute after temperature shift-up). We reasoned that in the presence of 26E-10, the mutant Z-ring may not be as robust as the wild-type ring at the permissive temperature of 30° C. and the inherent weakness of the mutant ring may be exacerbated.

We assessed the sensitivity of the ftsZ84 mutant strain DRC40 (harboring the plasmid vector pBR322) to 26E-10 at 30° C. in comparison to the congenic parent DRC39. Both DRC39 and DRC40 lack the major multidrug efflux pump AcrAB.

Whereas the MIC of 26E-10 for DRC39 is 10 µM, it was between 2.5 to 5 µM for DRC40. The DRC40 cell density at 2.5 µM compound was very low compared to the untreated control, with predominantly long filaments (16×), filamentous ghosts, and few short cells present (FIG. 20). DRC40 showed absolutely no growth at 5 µM, whereas DRC39 had a mixture of filaments of varying lengths and short cells present at a low density at this concentration of 26E-10. The cell density of DRC39 at 5 µM was appreciably higher than that of DRC40 at 2.5 µM. These results indicate that the ftsZ84 mutant (DRC40) has higher sensitivity toward 26E-10 compared to its wild-type parent (DRC39), likely because the presence of 26E-10 augments the inherent weakness of the ftsZ84 ring structure, akin to a synthetic lethal genetic interaction.

Whether the higher sensitivity of ftsZ84 to 26E-10 could be reversed in the presence of the recombinant pBR322 plasmid carrying the wild-type ftsZ gene was also tested. Indeed, when wild-type ftsZ was provided in trans, the MIC of 26E-10 for the mutant DRC40 was 10 µM, identical to that seen with the DRC39 parental cells. DRC40/pBR-ftsZ$^+$ cells underwent robust cell division at 2.5 µM 26E-10, unlike the situation with DRC40/pBR322. Moreover, at 5 µM 26E-10, there was higher cell density and less pronounced filamentation with DRC40/pBR-ftsZ$^+$ in contrast to DRC40/pBR322. These results provide compelling genetic evidence that 26E-10 perturbs FtsZ rings in vivo.

Effect of Compound on FtsZ Ring Thermolability

In addition, the phenotype of ftsZ84 cells was examined in the presence of 26E-10 over time to determine the thermolability of the ftsZ84 rings. Specifically, the phenotype of the thermosensitive ftsZ84 was assessed at 30° C., and also at 42° C. at 10 and 120 minutes. At 42° C. the mutant FtsZ rings were rapidly destabilized, within 10 minutes. A similar phenotype is expected with small molecules that inhibit or activate polymerization-dependent FtsZ GTPase activity.

ZipA interacts with FtsZ both in vitro and in vivo and it has been shown that a second copy of zipA can suppress the thermosensitivity of the ftsZ84 mutant at the restrictive temperature of 42° C. This is because ZipA is a stabilizer of FtsZ ring assembly and doubling the number of ZipA molecules in the cell leads to the stabilization of the thermolabile FtsZ84 ring in vivo.

A second copy of the essential division gene zipA can also decrease or ameliorate the toxicity of 26E-10. The fact that a second copy of zipA can reverse the toxicity of 26E-10 to a significant degree suggests that 26E-10 may be destabilizing the FtsZ ring structure in vivo.

Example 4

Screening for Cell Division Inhibitors and FtsZ-Interacting Compounds Using Small Molecule Microarrays Small molecule libraries are printed on glass slides to create small molecule microarrays to provide an opportunity to explore the feasibility of using such microarrays to identify FtsZ interacting compounds, e.g., FtsZ agonists or antagonists. The microarray is created by using a high-precision robot to pick up a small volume of dissolved compounds from the original 384 well plates and repetitively deliver 1 nL of solution to defined locations on a chemically derivatized glass microscope slide. Each compound is immobilized on the glass slide via a covalent linkage between a common functional group on the small molecule and the maleimide-derivatized glass slides. Interactions between FtsZ and small molecules are determined by incubating the microarray slide with purified FtsZ-GFP fusion protein and then visualizing the location of the bound protein by the ArrayWoRx fluorescent slide scanner. This experiment is performed in the absence of GTP to identify compounds that bind FtsZ monomers and in the presence of GTP to identify compounds that bind FtsZ polymers. Data obtained from screening the microarray library may validate the initial hits identified in the enzyme-coupled biochemical screen and provide evidence for the utility of small molecule microarrays as a fast and efficient method for screening future chemical libraries. In other embodiments, cells are dispensed on a substrate either prior to or following arraying of test compounds on the substrate. The cells may be affixed on portions of a substrate that have been treated (e.g., derivatized) to render them cytophilic as described, for example, in U.S. Pat. Nos. 5,976,826 and 6,368,838. Cell growth and/or morphology can be assessed.

Screening a chemical library in a microarray format may increase the speed of the screening method and also increases the reliability of the assay by comparing the hits identified by microarray analysis with those obtained from other in vitro and cell-based screening assays. In addition, the combination of the microarray assay with other assay methods will also assist in the validation of the targets identified, e.g., by comparing the targets identified in one assay to the targets identified in the other assay. Validation of inhibiting and activating structures is important for molecular modeling and generation of more potent derivatives against a given target.

Example 5

Combination Anti-Bacterial Treatment

The present Example demonstrates that combinations of anti-bacterial molecules identified using the in vitro and/or in vivo assays described herein can be used at sub-lethal concentrations (of each agent) as effective anti-bacterial treatments.

Bacterial cells (*E. coli* strain DRC39) were exposed to sub-lethal concentrations, i.e., concentrations below the minimum inhibitory concentration (MIC), of six different agents that inhibit FtsZ GTPase activity (as determined by in vitro tests) in combination with varying concentrations of either of two different inhibitors of cell division that induce cell filamentation and death without apparently affecting FtsZ GTPase activity in any significant way, at the concentrations tested.

The compounds that inhibit FtsZ GTPase activity, referred to as FtsZ GTPase activity inhibitors, were 27D-12, 27F-02, 16L-09, 58P-18, 5C-16, and 7N-12; their minimum inhibitory concentrations (MICs) against DRC39 cells are 20 µM, 5 µM, 10 µM, 80 µM, 2.5 µM, and 1.25 µM, respectively (see also FIG. 19). The other cell division inhibitors used in the experiments, which apparently do not affect FtsZ GTPase activity at the concentrations tested, were 26E-10 and 3G-09. Their MICs against DRC39 cells are 10 µM and 6 µM, respectively. These inhibitors are described above and in U.S. Ser. No. 10/153,268, filed May 22, 2001 and U.S. Ser. No. 10/180, 348, filed Jun. 26, 2001.

In a first experiment, cells were cultured in culture tubes in medium containing 1 µM of 27F-02 in combination with 5 µM or 2.5 µM or 1.25 µM 26E-10. Cell growth was assessed by visual inspection of cells incubated in culture tubes in this experiment and in the second, third, and fourth experiments described in this Example. In the fifth experiment growth was measured by reading optical density ($OD_{600}$) using a multi-well plate reader. Cells were inoculated at a low concentration ($1-2\times10^5$ cells/ml), such that the medium appeared clear. Cell growth resulted in visible turbidity, while medium in tubes in which cells failed to grow remained clear. Cells exposed to the foregoing combinations failed to detectably grow at all. Thus concentrations of 27F-02 5-fold lower than the 27F-02 MIC were inhibitory when combined with 26E-10 at concentrations ranging from 2 to 8-fold below the MIC of 26E-10. It was found that cells exposed to 0.5 µM 27F-02 in combination with 1.25 µM 26E-10 grew fairly well (~75% of either 0.5 µM 27F-02 or 1.25 µM 26E-10 only controls, as assessed by visual inspection of turbidity).

In a second experiment 2.5 µM of 16L-09 in combination with either 5 µM or 2.5 µM of 26E-10 killed DRC39 cells (no visible turbidity in cultures). Thus a 4-fold reduction in the MIC of 16L-09 resulted when the compound was administered in combination with 26E-10 at 2 to 4-fold lower concentrations than the 26E-10 MIC. However, 2.5 µM of 16L-09 failed to cause any significant growth inhibition in combination with a still lower concentration (1.25 µM) of 26E-10.

In a third experiment, 40 µM of 58P-18 in combination with 5 µM of 26E-10 resulted in killing of DRC39 cells, whereas the same concentration of 58P-18 together with 2.5 µM of 26E-10 did not completely inhibit cell growth. Again, a reduction in the MIC of both compounds (in both cases by a factor of 2 or more) was achieved by administering the compounds in combination. The combination of 40 µM 58P-18 and 2.5 µM 26E-10 allowed ~30% to 50% of the amount of growth that occurred in the presence of either single inhibitor at the same concentration (i.e., 40 µM 58P-18 or 2.5 µM 26E-0).

In a fourth experiment, 5 or 10 µM of 27D-12 was combined with 2.5 µM or 5 µM of 26E-10. No significant cell lethality was observed.

In a fifth experiment, 5 µM 26-E10 in combination with 1.25 µM 5C-16 caused 88% growth inhibition (12% of the amount of growth in the absence of compound), while growth inhibition in the presence of 26E-10 and 5C-16 singly at these concentrations were 59% and 15% respectively (41% and 85% of the amount of growth in the absence of compound, respectively). 0.375 µM 3G-09 caused 8% growth inhibition, and 1 µM 5C-16 caused 0% growth inhibition when used alone (92% and 100% of the amount of growth in the absence of compound respectively), whereas the combination resulted in 90% growth inhibition (10% of the amount of growth in the absence of compound).

A combination of two FtsZ GTPase activity inhibitors, 5C-16 and 7N-12, was also tested. A concentration of 0.3 µM 7N-12 in combination with 1 µM 5C-16 caused 58% growth inhibition (42% of the amount of growth in the absence of compound), whereas the same concentrations of compounds when used individually resulted in 2% inhibition and 0% inhibition, respectively (98% and 100% of the amount of growth in the absence of compound). While not wishing to be bound by any theory, the level of synergistic inhibition appeared to be significantly lower than that typically observed with binary combinations containing one FtsZ GTPase inhibitor and one cell division inhibitor that does not appear to inhibit FtsZ GTPase activity.

The results described above show that various combinations including any of six FtsZ GTPase inhibitors and either of two cell division inhibitors that apparently do not affect FtsZ GTPase activity prevent or inhibit cell survival (i.e., kill cells) or proliferation at concentrations of each inhibitor that are significantly lower than their individual MICs. The results therefore support the utility of administering combinations of compounds, each at sub-MIC concentrations, to treat and/or prevent bacterial infections or to inhibit bacterial growth in other settings (e.g., as disinfectants).

Other embodiments of the invention will be apparent to those skilled in the art from a consideration of the specification or practice of the invention disclosed herein. It is intended that the specification and examples be considered as exemplary only, with the true scope and spirit of the invention being indicated by the claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more elements, limitations, clauses, descriptive terms, etc., from one or more of the claims is introduced into another claim unless the context or description indicates otherwise. Any claim that is dependent on another claim can be modified to include one or more elements, limitations, clauses, or descriptive terms found in any other claim that is dependent on the same base claim unless the context or description indicates otherwise. Furthermore, where the claims recite a composition, it is to be understood that methods of administering the composition, methods of using the composition for any of the purposes disclosed herein, and methods of making the composition are encompassed within the scope of the invention, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

Any of the embodiments of the invention that include administering a composition to a subject can include a step of providing a subject, e.g., a subject at risk of or suffering from a disease, disorder, or condition. "Providing a subject suffering from or at risk of a condition" is intended to indicate that a compound or composition is administered to a subject known or suspected to be suffering from the disease, disorder, or condition, or at increased risk of developing the disease, disorder, or condition relative to an average member of the population and is intended to indicate that the composition is administered for purposes of treating or preventing the disease, disorder, or condition and should not otherwise be construed as limiting the invention. The methods may include a step of identifying, e.g., diagnosing, a subject as suffering from or at risk of a disease, disorder, or condition. The disease, disorder, or condition may be, e.g., a disease, disorder, or condition caused by an infectious agent such as a bacterium.

Where ranges are given herein, endpoints are included. Unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it should be understood that any one or more compounds, diseases, conditions, or other claim elements may be explicitly excluded from any one or more of the claims. For purposes of brevity, these various embodiments in which one or more compounds, diseases, conditions, or other claim elements is/are excluded from the claims are not set forth individually herein but are included in the invention.

What is claimed is:

1. A method for identifying a preferred combination of compounds that affects cell growth or division, comprising steps of:
  contacting bacteria with two candidate compounds comprising a first compound provided at a first concentration that is below its minimum inhibitory concentration (MIC) and a second compound provided at a second concentration that is below its MIC, and wherein at least one of the candidate compounds inhibits bacterial cell division when provided at a concentration at or above its MIC;
  measuring bacterial survival or growth;
  identifying the compound combination as a preferred compound combination if bacterial survival or growth is decreased by the two candidate compounds more than by the first candidate compound when provided at the first concentration or by the second candidate compound when provided at the second concentration and wherein at least one of the candidate compounds inhibits FtsZ GTPase activity.

2. The method of claim 1, wherein one of the candidate compounds does not inhibit FtsZ GTPase activity.

3. The method of claim 1, wherein one of the candidate compounds does not inhibit FtsZ GTPase activity and one of the candidate compounds inhibits FtsZ GTPase activity.

4. The method of claim 1, wherein the bacteria express a mutant FtsZ protein.

5. The method of claim 1, wherein the step of measuring bacterial survival or growth comprises detecting a defect in cell division.

6. The method of claim 1, wherein the step of measuring bacterial survival or growth comprises detecting a defect in cell division by examining the bacteria microscopically.

* * * * *